US012702639B2

(12) United States Patent
Showalter et al.

(10) Patent No.: US 12,702,639 B2
(45) Date of Patent: Aug. 11, 2026

(54) THIOL-MICHAEL ADDITION HYDROGEL-BASED BRACHYTHERAPY SYSTEM AND METHODS COMPRISING THE SAME

(71) Applicants: UNIVERSITY OF VIRGINIA PATENT FOUNDATION, Charlottesville, VA (US); VIRGINIA TECH INTELLECTUAL PROPERTIES, INC., Blacksburg, VA (US)

(72) Inventors: Timothy Norman Showalter, Charlottesville, VA (US); Timothy E. Long, Blacksburg, VA (US); Nicholas Moon, Greer, SC (US)

(73) Assignees: UNIVERSITY OF VIRGINIA PATENT FOUNDATION, Charlottesville, VA (US); VIRGINIA TECH INTELLECTUAL PROPERTIES, INC., Blacksburg, VA (US)

(*) Notice: Subject to any disclaimer, the term of this patent is extended or adjusted under 35 U.S.C. 154(b) by 1094 days.

(21) Appl. No.: 17/578,395

(22) Filed: Jan. 18, 2022

(65) Prior Publication Data

US 2022/0249366 A1 Aug. 11, 2022

Related U.S. Application Data

(63) Continuation-in-part of application No. 16/315,188, filed as application No. PCT/US2017/041156 on Jul. 7, 2017, now abandoned.

(60) Provisional application No. 62/359,400, filed on Jul. 7, 2016, provisional application No. 63/243,961, filed on Sep. 14, 2021.

(51) Int. Cl.

| | |
|---|---|
| ***A61K 9/00*** | (2006.01) |
| ***A61K 47/69*** | (2017.01) |
| ***A61L 31/14*** | (2006.01) |

(52) U.S. Cl.

CPC ........ *A61K 9/0024* (2013.01); *A61K 47/6903* (2017.08); *A61L 31/145* (2013.01)

(58) Field of Classification Search

None

See application file for complete search history.

(56) References Cited

U.S. PATENT DOCUMENTS

| | | | | |
|---|---|---|---|---|
| 6,248,057 B1 | | 6/2001 | Mavity et al. | |
| 6,958,212 B1 | * | 10/2005 | Hubbell | A61P 17/02 514/180 |
| 7,744,913 B2 | * | 6/2010 | Noyes | A61K 51/12 424/422 |
| 8,500,618 B2 | | 8/2013 | Isham | |
| 2005/0070753 A1 | | 3/2005 | Forman et al. | |
| 2006/0116546 A1 | | 6/2006 | Eng | |
| 2007/0299210 A1 | | 12/2007 | Kulshrestha et al. | |
| 2008/0288068 A1 | * | 11/2008 | Kronowitz | A61N 5/1015 623/8 |
| 2011/0142936 A1 | * | 6/2011 | Campbell | A61K 51/1244 424/484 |
| 2013/0053682 A1 | | 2/2013 | Esthappan et al. | |
| 2013/0204070 A1 | | 8/2013 | Makel et al. | |
| 2018/0311484 A1 | | 11/2018 | Lake et al. | |

FOREIGN PATENT DOCUMENTS

WO 2018009839 A1 1/2018

OTHER PUBLICATIONS

Small et al (Clinical outcomes with the MammoSite radiation therapy system: results of a prospective trial. J Radiat Oncol. Dec. 2015; 4(4): 395-400) (Year: 2015).*

Pritchard et al (An injectable thiol-acrylate poly(ethylene glycol) hydrogel for sustained release of methylprednisolone sodium succinate. Biomaterials. Jan. 2011; 32(2): 587-597) (Year: 2011).*

Czerner et al (Determination of Elastic Modulus of Gelatin Gels by Indentation Experiments. Procedia Materials Science 8 (2015) 287-296) (Year: 2015).*

Varian: "Varian Brachytherapy Applicators and Accessories," Jan. 1, 2011 (Jan. 1, 2011), XP055339041, Retrieved from the Internet: URL:https://www.varian.com/sites/default/files/resource_attachments/Brachytherapy_Applicators_Accessories_Catalogue_O_O.pdf.

Kirisits et al., "The Vienna applicator for combined intracavitary and interstitial brachytherapy of cervical cancer. Design, application, treatment planning, and dosimetric results," International Journal of Radiation: Oncology Biology Physics, Pergamon Press, USA, vol. 65, No. 2, Jun. 1, 2006 (Jun. 1, 2006), pp. 624-630, XP024898002, ISSN: 0360-3016, DOI: 10.1016/J.IJROBP.2006.01.036.

Liu et al (Dextran-based hydrogel formed by thiol-Michael addition reactionfor 3D cell encapsulation. Colloids and Surfaces B: Biointerfaces 128 (2015) 140-148) (Year: 2015).

International Search Report and Written Opinion of International Application No. PCT/US2022/025740, dated Jun. 17, 2022.

* cited by examiner

*Primary Examiner* — Jake M Vu

(74) *Attorney, Agent, or Firm* — RAPHAEL BELLUM PLLC

(57) ABSTRACT

The invention relates generally to methods of using a thiol-Michael addition hydrogel for providing intracavitary brachytherapy and/or displacing tissue and organs. The thiol-Michael addition hydrogel may be used as a packing material and an attenuation material for intracavitary brachytherapy applications. The invention also relates generally to a brachytherapy applicator, which may be used in conjunction with the thiol-Michael addition hydrogel and methods thereof. The invention also relates to a positioning device system for providing intracavitary brachytherapy treatment and a kit thereof.

22 Claims, 27 Drawing Sheets

Water Syringe
Applicator
Cavity
Reagent Syringe

THIOL-MICHAEL ADDITION HYDROGEL-BASED BRACHYTHERAPY SYSTEM AND METHODS COMPRISING THE SAME

CROSS REFERENCE TO RELATED APPLICATIONS

The application is a Continuation-in-Part of U.S. patent application Ser. No. 16/315,188, filed Jan. 4, 2019, which is a 35 U.S.C. § 371 of International Application No. PCT/US17/41156, filed Jul. 7, 2017, which claims the benefit of U.S. Provisional Patent Application No. 62/359,400, filed Jul. 7, 2016. This application also claims the benefit of U.S. Provisional Patent Application No. 63/243,961, filed Sep. 14, 2021. The entire contents of each of which are incorporated herein by reference.

BACKGROUND

Many cancer protocols utilize brachytherapy, a form of radiation therapy that proceeds by placing radioactive material temporarily near the tumor site. See Gerbaulet, European Society for Therapeutic Radiology and Oncology; *The GEC ESTRO handbook of brachytherapy*. ESTRO: Brussels, BE, 2002. Treatments for many pelvic cancers, including gynecological cancers such as cervical, uterine, and vaginal cancers, and rectal cancer, often include pelvic brachytherapy as either the definitive treatment or as an adjunct to surgery. Common techniques include vaginal cylinder brachytherapy used for adjuvant treatment to the vaginal cuff and upper vagina after hysterectomy for endometrial cancer treatment (see Small et al., *Brachytherapy* 2012, 11, 58-67) and tandem and ovoid brachytherapy used for the definitive treatment of cervical cancer (see Viswanathan et al., *Brachytherapy* 2012, 11, 33-46; Viswanathan et al., *Brachytherapy* 2012, 11, 47-52). Treatment planning utilizing technologies such as CT and MRI imaging allows medical professionals to selectively target tumor sites and significantly improves patient outcomes.

Most pelvic brachytherapy protocols utilize packing materials to stabilize the applicator within the pelvic cavity, such as, for example, the vagina, and displace healthy tissue, such as the bladder and rectum, to protect them from harmful radiation doses. See Viswanathan et al., *Brachytherapy* 2012, 11, 33-46. Despite significant improvements in the quality and sophistication of other aspects of brachytherapy treatments such as image-guided dosage planning and a transition from inpatient to outpatient procedures, improvements in packing materials lag. The use of gauze, originally developed in the context of general anesthesia during low dose-rate brachytherapy applications, results in significant patient discomfort during placement and removal. Further, the required use of forceps increases the risk of patient injury, such as vaginal laceration. A saline-filled balloon provides a commercially available alternative to gauze packing (Alatus®, Radiadyne, Houston, TX). See Xu-Welliver et al., *Pract. Radiat. Oncol.* 2013, 3, 263-8; Rockey et al., *J. Contemp. Brachytherapy* 2013, 5, 17-22. However, the high price of the single-use balloons, severely limits its adoption into wider clinical practice. The balloon also potentially crowds the applicators, interfering with applicator positioning while the rigid nature of the balloon fails to conform to the unique patient anatomy. For these reasons, balloon packing remains a suboptimal form of personalized vaginal packing for pelvic brachytherapy. To date, no simple, comfortable, customizable, and inexpensive packing material exists.

In addition, standard brachytherapy applicators have changed little over the past few decades, despite tremendous overall changes in brachytherapy treatment. See Harkenrider et al., *Int. J. Radiat. Oncol. Biol. Phys.* 2015, 92(4), 921-934. There is a need for improvement and innovation in pelvic brachytherapy applicators and accessories to enhance clinicians' ability to deliver personalized, time-efficient image-guided brachytherapy for patients who are treated as outpatients under mild sedation or conscious sedation and to harness the full potential of computerized treatment planning.

The invention addresses these needs.

SUMMARY OF THE INVENTION

This invention provides a new paradigm for intracavitary brachytherapy (e.g., pelvic brachytherapy) treatment based upon the use of a self-expanding thiol-Michael addition hydrogel to provide individualized intracavitary packing and create a personalized solution for intracavitary attenuation. No existing clinical radiation therapy procedure uses in situ polymer gel formation to fill a cavity, to serve as intracavitary packing, or as a personalized strategy for image-guided treatment. The invention accomplishes this by a hydrogel composition, method, applicator, and kit according to the invention, which provides a simple, readily applied solution to yield an improved, personalized strategy for image-guided brachytherapy treatment.

The invention relates to a thiol-Michael addition hydrogel and method thereof that can be used to improve the clinical care of patients receiving brachytherapy for intracavitary cancers, including gynecological and rectal cancers. The biocompatible hydrogel can form in situ after being injected into the intracavitary space, such as the pelvic cavity. Swelling of the hydrogel with water after gelation can be used to displace tissue. The hydrogel serves as intracavitary packing material during brachytherapy, including, for example, high-dose-rate brachytherapy, for pelvic and gynecological cancers (such as cervical cancer), displacing rectum and bladder, providing radiation attenuation, and stabilizing the brachytherapy applicator. For example, the thiol-Michael addition hydrogel of the invention can be used for vaginal packing for HDR brachytherapy using standard intracavitary GYN applicators (i.e., ring and tandem, tandem and ovoid, Y-applicator, intrauterine tandems) for brachytherapy applications in lieu of existing options. Current alternatives include packing the pelvic cavity, such as the vagina, with gauze, which is uncomfortable for patients, subject to errors and provides limited attenuation of radiation dose, and balloon packing systems that are expensive, cumbersome to use, and subject to interference between the applicator and packing device. The thiol-Michael addition hydrogel and method of the invention provides, among other things, a simple, customized strategy for packing a cavity in the body (e.g., the pelvic cavity or other bodily location for intracavitary treatment, either a natural cavity of the digestive or aerodigestive tract or one made surgically) for brachytherapy that provides attenuation and consistent imaging properties while improving patient comfort and limiting costs.

The invention thus relates to a method for displacing tissue and/or organs of a mammalian subject, comprising, consisting of, or consisting essentially of delivering a thiol-Michael addition hydrogel to a cavity of the body (e.g., the pelvic cavity or other bodily location for intracavitary treatment, either a natural cavity of the digestive or aerodigestive tract or one made surgically), expanding the thiol-Michael addition hydrogel, and displacing tissue and/or organs by the expanding thiol-Michael addition hydrogel.

The invention also relates to a method for providing intracavitary brachytherapy, comprising, consisting of, or consisting essentially of delivering a thiol-Michael addition hydrogel of the invention to a cavity of the body (e.g., the pelvic cavity or other bodily location for intracavitary treatment, either a natural cavity of the digestive or aerodigestive tract or one made surgically), expanding the thiol-Michael addition hydrogel, and displacing tissue and/or organs by the expanding thiol-Michael addition hydrogel.

The invention also relates to a method for providing intracavitary brachytherapy, comprising, consisting of, or consisting essentially of providing a brachytherapy applicator (e.g., a ring and tandem applicator, tandem and ovoid applicator, Y-applicator, intrauterine tandems applicator, brachytherapy needle applicator, and any other brachytherapy applicator designed to treat via intracavitary or interstitial methods) comprising a therapy delivery portion with one or more radioactive sources attached thereto, positioning the brachytherapy applicator at a static position in a cavity of the body (e.g., the pelvic cavity or other bodily location for intracavitary treatment, either a natural cavity of the digestive or aerodigestive tract or one made surgically), delivering a thiol-Michael addition hydrogel to the body cavity, expanding the thiol-Michael addition hydrogel, displacing tissue and/or organs by the expanding thiol-Michael addition hydrogel, and delivering the one or more radioactive sources to a target tissue region.

The invention also relates to a method providing intracavitary brachytherapy, comprising, consisting of, or consisting essentially of optionally providing a brachytherapy applicator (e.g., a ring and tandem applicator, tandem and ovoid applicator, Y-applicator, intrauterine tandems applicator, brachytherapy needle applicator, and any other brachytherapy applicator designed to treat via intracavitary or interstitial methods) comprising a therapy delivery portion with one or more radioactive sources attached thereto, optionally positioning the brachytherapy applicator at a static position in a cavity of the body (e.g., the pelvic cavity, such as the vagina or uterus, or other bodily location for intracavitary treatment, either a natural cavity of the digestive or aerodigestive tract or one made surgically), providing at least one container, positioning the at least one container inside the body cavity, delivering a thiol-Michael addition hydrogel to the inside of the at least one container present inside the body cavity, expanding the thiol-Michael addition hydrogel inside of the at least one container present inside the body cavity to conform the at least one container to the body cavity, optionally displacing tissue and/or organs by the expanding thiol-Michael addition hydrogel, optionally delivering the one or more radioactive sources to a target tissue region (e.g., performing radiation treatment planning and delivering radiation treatment), optionally lowering the modulus of the thiol-Michael addition hydrogel inside of the at least one container present inside the body cavity, and optionally extracting from the body cavity the brachytherapy applicator and/or the at least one container that contains the thiol-Michael addition hydrogel.

The invention also relates to a positioning device system for providing intracavitary brachytherapy treatment that may be used in the methods of the invention and which may come in the form of a kit.

The thiol-Michael addition hydrogel that may be used in the methods of the invention comprises, consists of, or consists essentially of the reaction product of any suitable at least one Michael acceptor and any suitable at least one thiol compound, reacted in the presence of an aqueous base. The thiol-Michael addition hydrogel, including its precursor materials, are described in further detail below.

The invention also relates to a rigid, reusable, 5-channel vaginal cylinder brachytherapy applicator, which may be used in conjunction with the thiol-Michael addition hydrogel and method of the invention, for intracavitary brachytherapy, including, for example, vaginal cuff brachytherapy after hysterectomy and for primary vaginal cancers, including endometrial cancer. The brachytherapy applicator of the invention improves upon existing options for intracavitary brachytherapy (e.g., pelvic brachytherapy) by providing a customized solution that conforms to patient anatomy and offers more precise radiation delivery while maintaining an efficient workflow. For example, the brachytherapy applicator of the invention dramatically improves the care of women receiving tandem-based brachytherapy for cervical cancer as well as adjuvant brachytherapy after hysterectomy for uterine cancers.

As used herein, "a," "an," "the," "at least one," and "one or more" are used interchangeably, The term "and/or" means one or all of the listed elements (e.g., an antiseptic skin preparation agent means one or more antiseptic skin preparation agents).

Also herein, the recitations of numerical ranges by endpoints include all numbers subsumed within that range (e.g., 1-5 includes 1, 1.5, 2, 2.75, 3, 3.80, 4, 5, etc.).

The above summary of the invention is not intended to describe each disclosed embodiment or every implementation of the invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1(*b*) shows exemplary liquid precursor materials filling the volume and conforming to the shape of the cavity.

FIG. 1(*c*) shows exemplary rapid gelation occurring to produce the packing material.

FIG. 1(*d*) shows an exemplary application of further tissue displacement by delivering water through a separate syringe.

FIG. 3(*b*) shows the effect of PEGDA molecular weight on equilibrium gel modulus of exemplary hydrogels of the invention.

FIG. 4(*b*) shows the effect of initial water content on equilibrium gel modulus of exemplary hydrogels of the invention.

FIG. 5(*b*) shows the effect base solution concentration on equilibrium gel modulus of exemplary hydrogels of the invention.

FIG. 6(*b*) shows the effect of base concentration and initial water content on water uptake of dried, extracted exemplary hydrogels of the invention.

FIG. 6(*c*) shows the effect of initial water content on water uptake of dried, extracted exemplary hydrogels of the invention.

FIG. 7(*b*) shows the volume change for undried, unextracted exemplary hydrogels of the invention with differing initial water content.

FIG. 10(*b*) shows an CT image of a hydrogel of the invention (1.2:1 thiol:acrylate, 50 wt % $H_2O$, 0.1M $NaHCO_3$) on a 15 mL scale, with a 0.6 mL Omnipaque solution.

FIG. 20(*b*) shows a thiol-Michael addition hydrogel of the invention expanded inside one of the 3D-printed phantoms.

DETAILED DESCRIPTION OF THE INVENTION

Figures 1A, 1B, 1C, 1D:
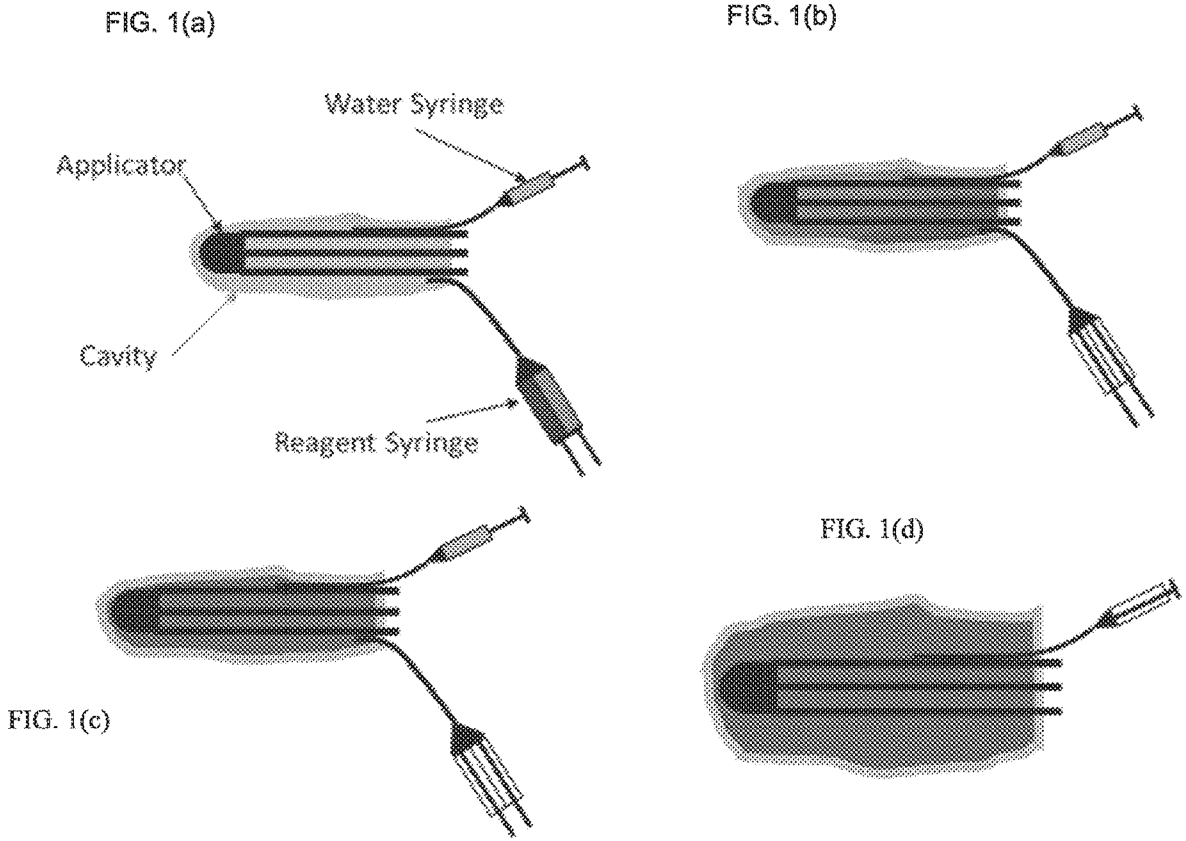
FIG. 1(*a*) shows an exemplary application of the hydrogel of the invention as a packing material for intracavitary brachytherapy.

The existing options for intracavitary packing (e.g., pelvic packing, including vaginal packing) suffer from a number of limitations and drawbacks. For example, one existing option—gauze—is uncomfortable for patients, has limited use for outpatients (was developed in an era of inpatient brachytherapy), and requires a prolonged insertion process involving manual packing of gauze strip with forceps. Another existing option—balloon packing device (i.e., Alatus® system by Radiadyne in Houston, TX)—is exceedingly expensive, crowds the device in vagina space due to 3 brachytherapy devices and 2 balloons with tubing, and the posterior balloon interferes with posterior edge of most common tandem applicator (Fletcher-Suit), which curves to contact posterior vaginal wall. The rectal "blade," another existing option, is difficult to place due to device crowding from vertical column of applicators and rectal blade, and does not displace the bladder.

Furthermore, the existing options for brachytherapy applicators, including, for example, vaginal cuff brachytherapy applicators, suffer from a number of limitations and drawbacks. For vaginal cylinder brachytherapy, for example, the standard single-channel design requires a range of sizes, restricts diameter flexibility, and provides little opportunity to sculpt radiation doses—a major limitation that is inconsistent with the widespread use of CT-based, 3-dimensional treatment planning. Furthermore, standard cylinders are subject to air pockets due to imperfect conformance to the vaginal cuff, and this can result in suboptimal dosimetry. See Small et al., *Brachytherapy* 2012, 11, 58-67; Richardson et al., *Int. J. Radiat. Oncol. Biol. Phys.* 2010, 78(1), 276-279. The custom acrylic vaginal mold technique (see Khoury et al., *Brachytherapy* 2015, 14(1), 51-55) is time consuming (alginate impression must first be made to create mold for acrylic), requires special training to make custom molds, and, while the mold conforms to vaginal apex, it must be inserted through narrower introitus. The diameter flexibility of the CET multichannel vaginal cylinder (see Demanes et al., *Int. J. Radiat. Oncol. Biol. Phys.* 1999, 44(1), 211-219) is restricted, and channel location near the cylinder surface increases hot spots on vaginal mucosa. Multi-channel applicators would provide increased control of radiation doses (see Demanes et al., *Int. J. Radiat. Oncol. Biol. Phys.* 1999, 44(1), 211-219; Khoury et al., *Brachytherapy* 2015, 14(1), 51-55), but cost and time efficiency is an important component of applicator development for routine, widespread use in vaginal cuff brachytherapy. Recognizing a need for improved technology in this area, Varian Medical Systems introduced a multi-channel alternative (Capri™ applicator). However, the Varian applicator has not been embraced by medical professionals for routine vaginal cuff brachytherapy, largely due to cost and time delays related to the need to image and re-plan for each individual treatment. The Varian applicator and the intravaginal, single channel balloon attempt to improve conformality through an inflatable outer balloon, but these designs have other limitations with respect to size, cost, and workflow (Capri™), and limited dose range and optimization. See Miller et al., *Gynecol. Oncol.* 2010, 116(3), 413-418.

The invention answers these limitations and drawbacks, and provides a superior method for intracavitary packing in combination with a thiol-Michael addition hydrogel and standard brachytherapy applicators, and also provides a superior applicator that surpasses existing brachytherapy applicators and which may also be used with the thiol-Michael addition hydrogel of the invention.

Thiol-Michael Addition Hydrogel

The thiol-Michael addition click reaction involves the base or nucleophile-catalyzed addition of a thiolate into an electron-deficient alkene (Scheme 1 below). See Nair et al., *Chem. Mater.* 2014, 26, 724-744; Allen et al., *Can. J. Chem.* 1964, 42, 2616-20. In Scheme 1, "R" can be any organic group (aliphatic or aromatic), "B" is a base, and "EWG" is an electron-withdrawing group (e.g., carbonyl, nitrile, sulfone, nitro, phosphonate). The reaction occurs rapidly, under mild conditions, quantitatively, tolerates most functional groups, and occurs in biologically-friendly solvents including water. See Kolb et al., *Angew. Chem. Int. Ed.* 2001, 40, 2004-2021. Among its many other uses, the thiol-Michael addition reaction finds significant application in hydrogel synthesis with precursors including poly(ethylene glycol) (PEG)-based materials (see Deshmukh et al., *Biomaterials* 2010, 31, 6675-6684; Fu et al., *J. Biomed. Mater. Res. Part A* 2011, 98A, 201-211), polysaccharides (see Hiemstra et al., *Macromolecules* 2007, 40, 1165-1173; Baldwin et al., *Polym. Chem.* 2013, 4, 133-143), polypeptides (see Lutolf et al., *Adv. Mater.* 2003, 15, 888-892; Lutolf et al., *Biomacromolecules* 2003, 4, 713-722; Rizzi et al., *Biomacromolecules* 2006, 7, 3019-3029; Salinas et al., *Macromolecules* 2008, 41, 6019-6026; Jo et al., *J. Biomed. Mater. Res. Part A* 2010, 93A, 870-877), and synthetic materials (see Rossow et al., *J. Am. Chem. Soc.* 2012, 134, 4983-4989). Common applications include drug-delivery (see Fu et al., *J. Biomed. Mater. Res. Part A* 2011, 98A, 201-211; Pitarresi et al., *Macromol. Biosci.* 2008, 8, 891-902; Koehler et al., *Biomaterials* 2013, 34, 4150-4158), tissue engineering (see Lutolf et al., *Adv. Mater.* 2003, 15, 888-892; Li et al., *Chem. Soc. Rev.* 2012, 41, 2193-2221), and tissue repair (see Hiemstra et al., *Macromolecules* 2007, 40, 1165-1173; Zustiak et al., *Biomacromolecules* 2010, 11, 1348-1357). Langer and coworkers disclosed an injectable hydrogel from PEGDA and a three-arm, PEG-based trithiol THIOCURE® ETTMP 1300 (abbreviated as THIOCURE) in phosphate-buffered saline (PBS). See Pritchard et al., *Biomaterials* 2011, 32, 587-597, which is incorporated herein by reference. The authors characterized the formation, degradation, swelling, and mechanical behavior of the resulting hydrogels. Further investigations focused on the kinetics of methylprednisolone release and the formation and swelling properties of related PEG-based trithiol for use as an injectable, non-swelling hydrogel. See O'Shea et al., *Adv. Mater.* 2015, 27, 65-72.

Scheme 1: Mechanism of the base-catalyzed thiol-Michael reaction

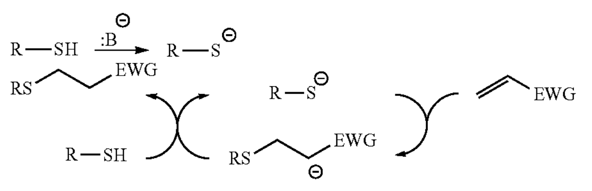

The invention relates to the use of a thiol-Michael addition hydrogel, a polymeric gel synthesized using a thiol-Michael addition click reaction, for application as a packing material and an attenuation material for intracavitary brachytherapy (e.g., pelvic brachytherapy) applications, resulting in attenuation and consistent imaging properties while improving patient comfort and limiting costs. This invention complements the application of thiol-Michael addition hydrogels known in the art and formed using thiol-Maleimide chemistry for other applications. See Phelps et al., *Adv. Mater.* 2012, 24(1), 64-70; Baldwin et al., *Polym. Chem.* 2013, 4(1), 133-143. The use of a thiol-Michael addition hydrogel for customized packing and attenuation for intracavitary brachytherapy applications is unprecedented. The hydrogel of the invention can act as a packing and attenuation material in conjunction with standard brachytherapy applicators for intracavitary and interstitial pelvic brachytherapy.

While any thiol-Michael addition hydrogel of the invention can potentially act as a packing material and an attenuation material for intracavitary brachytherapy (e.g., pelvic brachytherapy) applications, depending on its characteristics and properties, preferably, the thiol-Michael addition hydrogel of the invention comprises, consists of, or consists essentially of the reaction product of any suitable at least one Michael acceptor and any suitable at least one thiol compound, reacted in the presence of an aqueous base.

The Michael acceptor that may be used to make the thiol-Michael addition hydrogel of the invention includes, but is not limited to, acrylate, vinyl nitrile, vinyl nitro, vinyl phosphonate, vinyl sulfonate, and enone compounds. Preferably, the Michael acceptor is selected from an oligomeric poly(ethylene glycol) (PEG) diacrylate (PEGDA) having the following general structure:

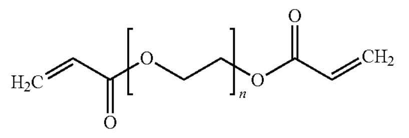

where n is an integer such that the PEGDA has an average molecular weight less than about 100,000 g/mol, for example, less than about 10,000 g/mol. While PEGDAs of virtually any molecular weight can be accessed synthetically, most of which may be used in the invention, preferred PEGDAs that may be used include, for example, $PEGDA_{250}$, $PEGDA_{575}$, and $PEGDA_{700}$, which are commercially available from Sigma Aldrich. PEG acrylates with more than three arms may also be used with a PEG dithiol, for example.

The thiol compound that may be used to make the thiol-Michael addition hydrogel of the invention includes, but is not limited to, any multi-arm, thiol terminated polymer with a backbone consisting of poly(ethylene glycol), polycaprolactam, poly(propylene glycol), and poly(lactide) chains, and any water-soluble polysaccharide functionalized with 3 or more thiol groups per chain. Preferably, the thiol compound is selected from a multi-arm, thiol-terminated PEG oligomer, such as, for example, a three-arm, thiol-terminated PEG oligomer, which has an average molecular weight less than about 100,000 g/mol, for example, less than about 10,000 g/mol. A preferred three-arm, thiol-terminated PEG oligomer that may be used in the invention is ethoxylated trimethylolpropane tri-3-mercaptopropionate, sold commercially as THIOCURE ETTMP 1300 (THIOCURE®) (Bruno Bock Thiochemicals).

The base that may be used to make the thiol-Michael addition hydrogel of the invention includes, but is not limited to, inorganic carbonates, inorganic bicarbonates, pH 7.4 or higher buffer, and amine bases (e.g., triethylamine, Hunig's base, DBU). Preferably, the base is $NaHCO_3$. The base is present in a concentration sufficient to catalyze the thiol-Michael addition reaction, for example, ranging from about 0.1 M to about 0.25 M, preferably about 0.175 M to about 0.25 M.

The thiol-Michael addition hydrogel of the invention can be prepared using a thiol:acrylate stoichiometric ratio (e.g., multi-arm, thiol-terminated PEG oligomer:PEGDA) ranging from about 1.8:1 to about 0.9:1. Preferably, the thiol:acrylate stoichiometric ratio is about 1:1. Also, a slight stoichiometric excess of thiol may result in more rapid hydrogel formation. The thiol-Michael addition hydrogel of the invention may have a water content ranging from about 25 wt % to about 75 wt %, including, for example, the gel may have a water content of about 50 wt %.

The multi-arm, thiol-terminated PEG oligomer may be first dissolved in a $NaHCO_3$ solution and then the PEGDA is added to the multi-arm, thiol-terminated PEG oligomer solution, leading to homogenous gel formation through a thiol-Michael addition reaction. Preferably, the thiol-Michael addition hydrogel of the invention comprises the reaction product of at least one PEGDA and THIOCURE® ETTMP 1300 (THIOCURE), reacted in the presence of catalytic quantities of aqueous $NaHCO_3$ (Scheme 2).

$NaHCO_3$) used in the reaction. Gelation is observed in less than 2 min for base concentrations as low as 0.1M. Formation of the hydrogel within 2 min after mixing the precursor materials ensures that the polymer gel can be formed on a clinically relevant timescale.

A thiol-Michael addition hydrogel of the invention may have a gel fraction of 80% or higher, for example, greater than 85%, greater than 90%, or greater than 95%. Gel fractions of 80% or higher indicate that the precursors are efficiently connected to the network. Gel fractions in excess of 90% reduces the risk of soluble fractions leaching into the body, rendering the polymeric gel suitable for clinical application. The gel fraction describes the extent to which the starting material incorporates into the final network. The gel fraction of the crosslinked materials of the invention may be further optimized by, for example, providing longer reaction times, tuning catalyst efficiency, and providing more time or higher temperature.

A thiol-Michael addition hydrogel of the invention may have a modulus sufficient to displace tissue, such as, for example, vaginal tissue and other internal organs, such as, for example, the rectum and bladder. The thiol-Michael addition hydrogel of the invention can be mechanically Scheme 2

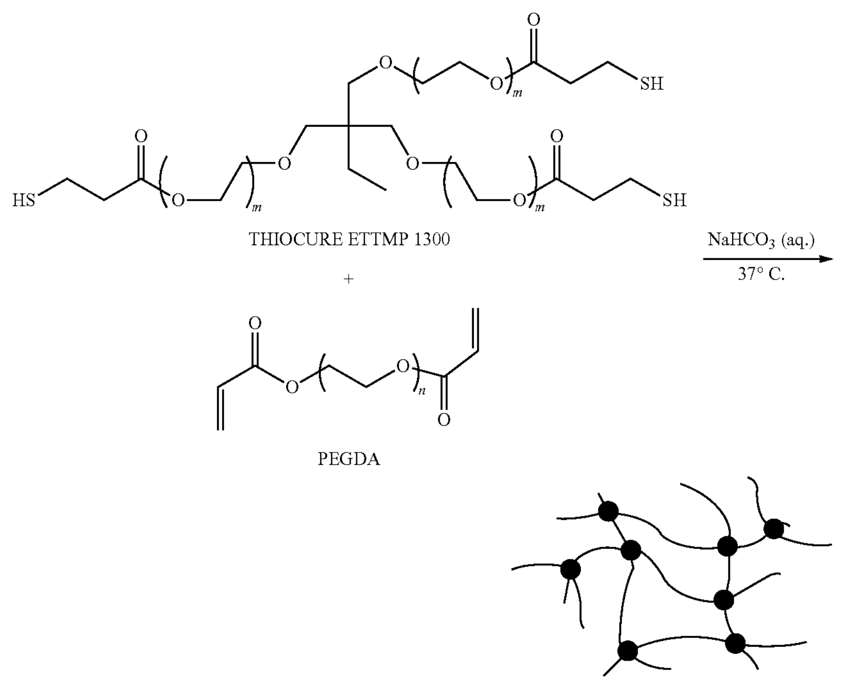

where m is an integer such that the THIOCURE has an average molecular weight of about 1,300 g/mol, and where n is an integer such that the PEGDA has an average molecular weight of about 250, 575, and/or 700 g/mol.

Varying formulation variables, including, for example, the PEGDA molecular weight, initial polymer concentrations, initial water content, and base concentration, allows for control of various hydrogel properties, including, for example, hydrogel-formation rate and modulus.

A thiol-Michael addition hydrogel of the invention may form in less than 2 min, preferably less than 90 sec. Gel formation time of the thiol-Michael addition hydrogel of the invention depends heavily on the concentration of base (e.g., durable, free-standing materials that can be readily manipulated, with shear moduli between about 10 and about 100 kPa, preferably about 10 kPa, which meets or exceeds the minimum requirements for displacing tissue. See Noakes et al., *J. Biomech.* 2008, 41, 3060-3065. For example, a storage modulus value of 10 kPa corresponds to the computed strength of the valsava contraction (see id.), and ensures that the hydrogels possess sufficient mechanical strength to support the applicator, displace tissue, and allow medical professionals to begin imaging procedures and treatment planning despite incomplete gel formation. As the brachytherapy treatment protocol usually lasts only about six hours, long-term hydrogel durability is less important. The thiol-Michael addition hydrogel may also reach a modulus of about 10 kPa in under 2 minutes (e.g., less than 90 seconds, less the 60 seconds, less than 45 seconds, etc.).

A thiol-Michael addition hydrogel of the invention can absorb additional water after gel formation, which can be used, for example, to fine-tune tissue displacement of tissue. Water can be used to further expand the gels in vivo after initial gelation using additional water delivered to the vagina. This water provides for the desired tissue displacement through isotropic swelling behavior of the polymeric gel. The ability of medical professionals to specifically tune the expansion of the hydrogel after gel formation provides an additional clinical benefit and control. A thiol-Michael addition hydrogel of the invention can absorb at least 2 times their mass of water at body temperature. A thiol-Michael addition hydrogel of the invention can also be softened prior to removal through the addition of sufficient water to lower the modulus of the gel, allowing for more comfortable removal. The swelling process reaches a reproducible, equilibrium that displays a swelling capacity based on the delivery water content, and subsequent addition of water softens the gel to allow removal from the vaginal cavity with simple extraction.

The heat generation during the formation of the thiol-Michael addition hydrogel of the invention can be maintained near 37° C. with an exotherm less than 10° C. Excess heat generation can be mitigated through the addition of water. A precursor material to the thiol-Michael addition hydrogel of the invention may also be delivered below room temperature (refrigerated) to mitigate heat evolution.

The Michael reaction is a well established synthetic methodology for protein conjugation in the absence of deleterious side reactions. Thiol-Michael addition hydrogel of the invention do not exhibit any immunological response in the majority of patients. For example, the hydrogel of the invention possess cytocompatibility based on biological evaluation against human vaginal epithelial cells.

The invention relates to a method for displacing tissue and/or organs of a mammalian subject, comprising, consisting of, or consisting essentially of delivering a thiol-Michael addition hydrogel to a cavity of the body (e.g., the pelvic cavity or other bodily location for intracavitary treatment, either a natural cavity of the digestive or aerodigestive tract or one made surgically), expanding the thiol-Michael addition hydrogel, and displacing tissue and/or organs by the expanding thiol-Michael addition hydrogel.

The invention also relates to a method for providing intracavitary brachytherapy, comprising, consisting of, or consisting essentially of delivering a thiol-Michael addition hydrogel of the invention to a cavity of the body (e.g., the pelvic cavity or other bodily location for intracavitary treatment, either a natural cavity of the digestive or aerodigestive tract or one made surgically), expanding the thiol-Michael addition hydrogel, and displacing tissue and/or organs by the expanding thiol-Michael addition hydrogel.

The invention also relates to a method for providing intracavitary brachytherapy, comprising, consisting of, or consisting essentially of providing a brachytherapy applicator (e.g., a ring and tandem applicator, tandem and ovoid applicator, Y-applicator, intrauterine tandems applicator, brachytherapy needle applicator, and any other brachytherapy applicator designed to treat via intracavitary or interstitial methods) comprising a therapy delivery portion with one or more radioactive sources attached thereto, positioning the brachytherapy applicator at a static position in a cavity of the body (e.g., the pelvic cavity or other bodily location for intracavitary treatment, either a natural cavity of the digestive or aerodigestive tract or one made surgically), delivering a thiol-Michael addition hydrogel to the body cavity, expanding the thiol-Michael addition hydrogel, displacing tissue and/or organs by the expanding thiol-Michael addition hydrogel, and delivering the one or more radioactive sources to a target tissue region.

The invention also relates to a method providing intracavitary brachytherapy, comprising, consisting of, or consisting essentially of:

optionally providing a brachytherapy applicator (e.g., a ring and tandem applicator, tandem and ovoid applicator, Y-applicator, intrauterine tandems applicator, brachytherapy needle applicator, and any other brachytherapy applicator designed to treat via intracavitary or interstitial methods) comprising a therapy delivery portion with one or more radioactive sources attached thereto, optionally positioning the brachytherapy applicator at a static position in a cavity of the body (e.g., the pelvic cavity, such as the vagina or uterus, or other bodily location for intracavitary treatment, either a natural cavity of the digestive or aerodigestive tract or one made surgically), providing at least one container, positioning the at least one container inside the body cavity, delivering a thiol-Michael addition hydrogel to the inside of the at least one container present inside the body cavity, expanding the thiol-Michael addition hydrogel inside of the at least one container present inside the body cavity to conform the at least one container to the body cavity, optionally displacing tissue and/or organs by the expanding thiol-Michael addition hydrogel, optionally delivering the one or more radioactive sources to a target tissue region, optionally lowering the modulus of the thiol-Michael addition hydrogel inside of the at least one container present inside the body cavity, and optionally extracting from the body cavity the brachytherapy applicator and/or the at least one container that contains the thiol-Michael addition hydrogel.

Preferably, the invention is directed to a method providing intracavitary brachytherapy, comprising, consisting of, or consisting essentially of:

providing a brachytherapy applicator (e.g., a ring and tandem applicator, tandem and ovoid applicator, Y-applicator, intrauterine tandems applicator, brachytherapy needle applicator, and any other brachytherapy applicator designed to treat via intracavitary or interstitial methods) comprising a therapy delivery portion with one or more radioactive sources attached thereto, positioning the brachytherapy applicator at a static position in a cavity of the body (e.g., the pelvic cavity, such as the vagina or uterus, or other bodily location for intracavitary treatment, either a natural cavity of the digestive or aerodigestive tract or one made surgically), providing at least one container, positioning the at least one container inside the body cavity, delivering a thiol-Michael addition hydrogel to the inside of the at least one container present inside the body cavity, expanding the thiol-Michael addition hydrogel inside of the at least one container present inside the body cavity to conform the at least one container to the body cavity, displacing tissue and/or organs by the expanding thiol-Michael addition hydrogel, delivering the one or more radioactive sources to a target tissue region (e.g., performing radiation treatment planning and delivering radiation treatment), optionally lowering the modulus of the thiol-Michael addition hydrogel inside of the at least one container present inside the body cavity, and optionally extracting from the body cavity the brachytherapy applicator and/or the at least one container that contains the thiol-Michael addition hydrogel.

In the methods of the invention, the cavity of the body includes, but is not limited to, the pelvic cavity (e.g., vagina, uterus, and rectum); the organ includes, but is not limited to, the bladder and rectum; the brachytherapy applicator may be positioned inside the body cavity before, at the same time, or after one or more containers are positioned inside the body cavity (e.g., the brachytherapy applicator is positioned inside the body cavity and then at least one container is positioned inside the body cavity, or at least one container is positioned inside the body cavity and then the brachytherapy applicator is positioned inside the body cavity, or at least one container is positioned inside the body cavity, then the brachytherapy applicator is positioned inside the body cavity, and then at least one additional container is positioned inside the body cavity, etc.); the precursor materials of the thiol-Michael addition hydrogel may be delivered to the cavity of the body or to the at least one container present inside the body cavity separately (e.g., one or more of the precursor materials may be delivered to the cavity of the body or the at least one container separately from one or more of the other precursor materials); the precursor materials of the thiol-Michael addition hydrogel may be reacted in the cavity of the body or the at least one container present inside the body cavity to form the thiol-Michael addition hydrogel; the delivering of the thiol-Michael addition hydrogel to the cavity of the body step or the at least one container present inside the body cavity step may comprise forming the thiol-Michael addition hydrogel inside the cavity of the body or the at least one container, respectively; the tissue and/or organs may be displaced away from one or more radioactive sources attached to a brachytherapy applicator; the thiol-Michael addition hydrogel may be expanded in the cavity of the body or the at least one container present inside the body cavity by adding water or saline solution to the gel; the modulus of the thiol-Michael addition hydrogel in the cavity of the body or the at least one container present inside the body cavity may be lowered, for example, by adding water or saline solution to the gel in an amount sufficient to lower the modulus of the gel; the thiol-Michael addition hydrogel or the at least one container present inside the body cavity may be extracted from the cavity of the body (lowering of the modulus of the thiol-Michael addition hydrogel may assist in extraction); the at least one container present inside the body cavity may be extracted from the body cavity before, simultaneously, or after the brachytherapy applicator is extracted from the body cavity; radiation treatment planning may be performed; radiation treatment may be delivered; and/or the thiol-Michael addition hydrogel or the at least one container present inside the body cavity can substantially surround the brachytherapy applicator, which may, for example, further immobilize the applicator.

As discussed, while the thiol-Michael addition hydrogel of the invention can be delivered to the cavity of the body or the at least one container present inside the body cavity after the precursor materials are combined, but preferably before gelation occurs, preferably, the precursor material of the thiol-Michael addition hydrogel (e.g., the oligomeric polyethylene glycol (PEG) diacrylate, the multi-arm, thiol-terminated PEG oligomer, and the aqueous base) can be delivered separately to the cavity of the body or the at least one container present inside the body cavity by any means known to one skilled in the art and combined and reacted in vivo in the cavity or the at least one container. For example, when the at least one container is positioned inside the body cavity, the thiol-Michael addition hydrogel of the invention can be delivered to the inside of the at least one container present inside the body cavity after the precursor materials are combined. However, preferably, the precursor materials are delivered, together or separately, to the at least one container inside the body cavity, and the precursor materials are then reacted inside of the at least one container present inside the body cavity to form the thiol-Michael addition hydrogel. The precursor materials present inside of the at least one container present inside the body cavity may be expanded by adding water and/or saline solution to the gel. The modulus of the thiol-Michael addition hydrogel inside of the at least one container present inside the body cavity may be lowered by adding water or saline solution to the gel in an amount sufficient to lower the modulus of the thiol-Michael addition hydrogel. The at least one container inside the body cavity may substantially surround the brachytherapy applicator inside the body cavity.

Delivery of the precursor materials to the body cavity or to the at least one container present inside the body cavity can be accomplished by any route accepted as appropriate by the medical community, and is not limited to any particular route. For example, in a method of the invention (shown in FIG. 1), the brachytherapy applicator and separate syringes housing the PEGDA, for example, and multi-arm, thiol-terminated PEG oligomer, for example, precursor materials are inserted into the pelvic cavity (or at least one container present inside the body cavity), for example, the vagina (FIG. 1(*a*)). The aqueous base, for example, $NaHCO_3$, may be in either or both syringes containing the precursor material, and/or it may delivered by a separate syringe from the precursor materials. After insertion, the precursor materials are delivered to the pelvic cavity (or at least one container present inside the body cavity) by injection of the syringes, where they are then mixed. The liquid precursor materials fill the volume and conform to the shape of the cavity (FIG. 1(*b*)). Rapid gelation occurs, furnishing the desired packing material in a simple and efficient manner (FIG. 1(*c*)). As the initial hydrogel of the invention may possess a water content below its equilibrium value, a medical professional may achieve further tissue displacement by delivering additional water through a separate syringe (FIG. 1(*d*)).

As discussed above, one of the methods of the invention is to deliver the hydrogel precursor materials to the inside of the at least one container present inside the body cavity. One purpose of this method is to displace the body tissue (e.g., the vaginal wall and adjacent pelvic tissues) during radiation therapy planning and delivery, to reduce dose to adjacent tissues by attenuation of radiation dose, and to stabilize radiation treatment equipment during radiation therapy planning and delivery. The at least one container, containing the hydrogel, may surround the brachytherapy applicator and conform to the body cavity (e.g., vaginal cavity), fitting any size or shape cavity. The reaction may occur within the at least one container that allows the gel to form into the shape of the body cavity (e.g., vaginal cavity) during the reaction. The placement of the hydrogel device may be performed as a separate procedure outside of brachytherapy applicator insertion, computed tomography and/or magnetic resonance imaging exam, radiation treatment planning, and radiation treatment delivery. The at least one container is intended to be in place temporarily inside the body cavity and removed after less than 24 hours. While the at least one container should not remain inserted into the patient for any time longer than required for radiation treatment, it can be left in the cavity for a longer time, if necessary. The positioning device system (discussed in more detail below) used in this method of the invention may include a tube available for the physician or other healthcare professional to inject saline prior to removing the hydrogel packing in cases where a softer or fractured hydrogel would help with extraction of the packing. These design characteristics optimize the packing performance of the hydrogel, allow fine-tuning by the physician (saline port), and maximize patient comfort. Physicians will have the option to use 1, 2, or more positioning device systems per patient, depending on the patient anatomy and needs for the treatment plan. As discussed below, the positioning device system, including the at least one container, may be present as a kit.

Figure 20A:
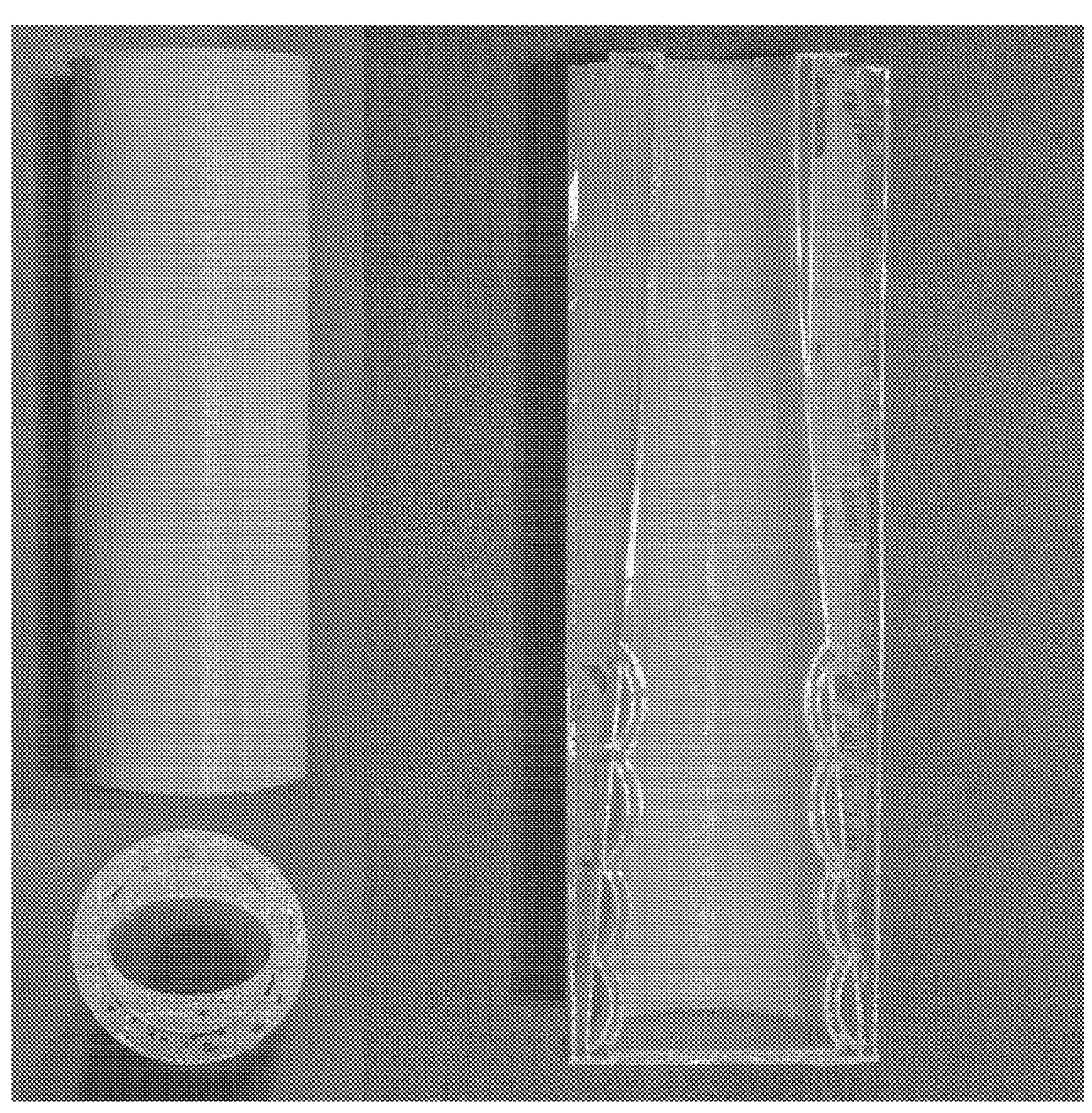
FIG. 20(*a*) shows 3D-printed phantoms designed to simulate anatomical variations (e.g., within a body cavity).
Figure 20B:
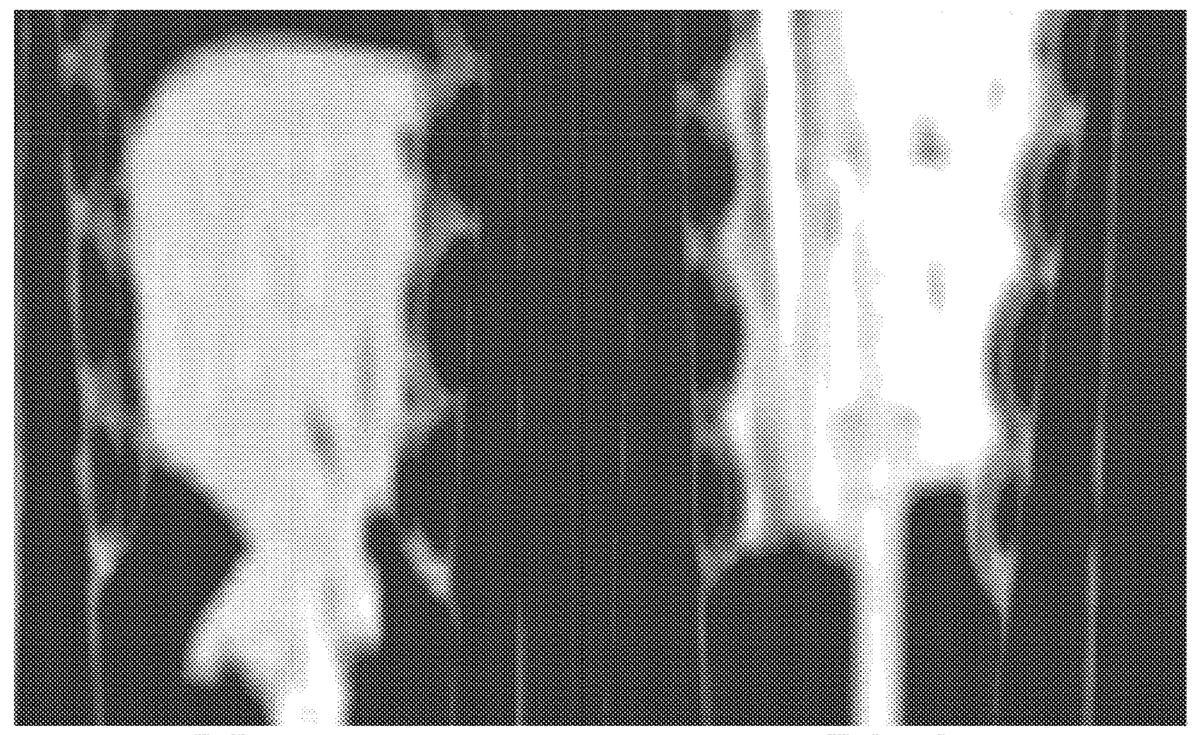

One of the improvements provided by this invention is that the hydrogel of the invention will adopt and conform to any body cavity. For example, as shown in FIG. 20(*a*) and FIG. 20(*b*), a thiol-Michael addition hydrogel of the invention expanded inside a 3D-printed phantom designed to simulate anatomical variations (e.g., within a body cavity) conforms and substantially fills the varied contours of the phantom (right-side picture of FIG. 20(*b*)), while a commercial balloon, such as the balloon used in the MammoSite® system, does not conform and substantially fill the same contours (left-side picture of FIG. 20(*b*)). For this reason, the container positioned inside the body cavity for use in the method of the invention should have physical characteristics that allow it, like the hydrogel expanded inside of it, to conform and substantially fill the varied contours of each patient's distinct body cavity. While any container known in the art may be used in the method of the invention, preferably, the container is a reaction bag/fill balloon, oversized compared to the hydrogel (e.g., a container capacity ranging from about 60-120, 70-110, 80-100, or 85-95 mL, preferably about 80 mL, compared to a hydrogel volume ranging from about 30-90, 40-80, 50-70, 55-65 mL, preferably about 50 mL), made of a thin (e.g., a thickness of about 1-6 mil, 2-5 mil, 3-4 mil, preferably about 4.4 mil), lightweight material (e.g., polyethylene) that minimally constrains the gelation, and/or is designed to permit the hydrogel to assume the shape of the cavity during reaction (e.g., the container modulus may match that of the gel to ensure good conformability within the body cavity). For example, a container that may be used in the methods of the invention may be made of a polyethylene material, have a flexural modulus ranging from about 4000-10000, 5000-9000, or 6000-8000 psi; an ultimate tensile ranging from about 2000-8000, 3000-7000, or 4000-6000 psi; an ultimate elongation ranging from about 300-600%, 350-550%, or 400-500%, and a tensile modulus at 100% elongation ranging from about 500-900, 550-850, or 600-800 psi, at 200% elongation ranging from about 900-1400, 950-1350, or 1000-1300 psi, and 300% elongation ranging from about 1400-1700, 1450-1650, or 1500-1600 psi. A preferred polyethylene reaction bag/fill balloon well-suited for the methods of the invention includes Polyzen, Inc.'s Medical Grade Polyether Thermoplastic Polyurethane (TPU) 90 Shore A Film at 2.2 mil, which has a hardness of 90 A, a flexural modulus of 7500 psi, an ultimate tensile of 5500 psi, an ultimate elongation of 450%, and a tensile modulus at 100%, 200%, and 300% elongation of 700, 1000, and 1500 psi, respectively.

In addition, the methods of the invention offers numerous advantages over current alternatives, such as the balloon and gauze methods of packing. Using PEG as the polymer for the hydrogel takes advantage of its biocompatibility and approval for implantation in the body by the FDA. See O'Shea et al., *Adv. Mater.* 2015, 27, 65-72; Yom-Tov et al., *Eur. Polym. J.* 2016, 74, 1-12. The proposed hydrogel features inexpensive precursor materials, which readily facilitates adoption by less-specialized clinics, including those in underdeveloped countries. Unlike balloons, hydrogel formation with the applicator in place provides a uniform and customized packing solution that conforms to the contours of the individual patient anatomy. Compared to gauze, which requires forceps for placement, the liquid state of the initially-injected precursor materials will significantly increase patient comfort during installation, since controllable gel-time allows the solution precursor materials to conform to the pelvic cavity space before setting, while the relatively low modulus allows for facile and more comfortable removal. Unlike the gauze method, the hydrogel also does not overly dry the mucosal membranes. Self-expansion of the gels of the invention provides customized packing and tissue displacement with less dependence on medical professional performance than gauze packing, preventing potential errors in packing. Patient comfort is also increased due to the limited exothermic reaction or contained absorption of heat through the composition of the hydrogel of the invention. The method of the invention also provides for a range of mechanical pressure to displace tissue and adjacent organs, such as the bladder and the rectum. The thiol-Michael addition hydrogel of the invention provide for attenuation of radiation due to electron density near that of water, which reduces the exposure of adjacent tissues to high radiation doses. Further, unlike alternative packing approaches, the thiol-Michael addition hydrogel of the invention are readily identified on CT and MRI, and distinguishable from brachytherapy applicators, water, tissue, and air, which is vital for image-guided treatment planning. The reaction of the precursor materials of the thiol-Michael addition hydrogel can also occur in the presence of imaging contrast material.

The invention also relates to a positioning device system for providing intracavitary brachytherapy treatment comprising, consisting essentially of, or consisting of at least one receptacle delivery device, a catheter device assembly, and a container. The receptacle delivery device contains and delivers the thiol-Michael addition hydrogel or at least one precursor material of the thiol-Michael addition hydrogel (e.g., at least one syringe). For example, the receptacle delivery device may comprise a first syringe containing at least one Michael acceptor and a second syringe containing at least one thiol compound.

The at least one receptacle delivery device and the container may be attached to the catheter device assembly. For example, the at least one receptacle delivery device may be attached to one end of the catheter device assembly and the container may be attached to other end of the catheter device assembly. Optionally, a structure, such as tubing connector, may connect the at least one receptacle delivery device to the catheter device assembly.

Figure 12:
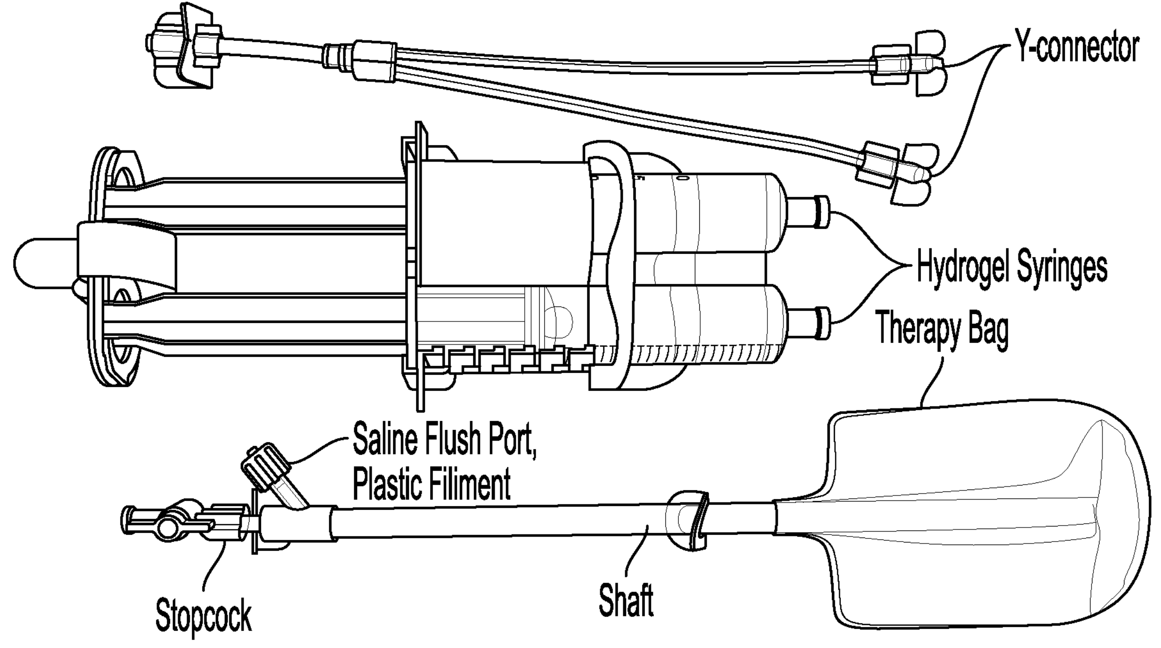
FIG. 12 shows exemplary components of the positioning device system of the invention, including a Y-connector, hydrogel syringes, and catheter device assembly.
Figure 13:
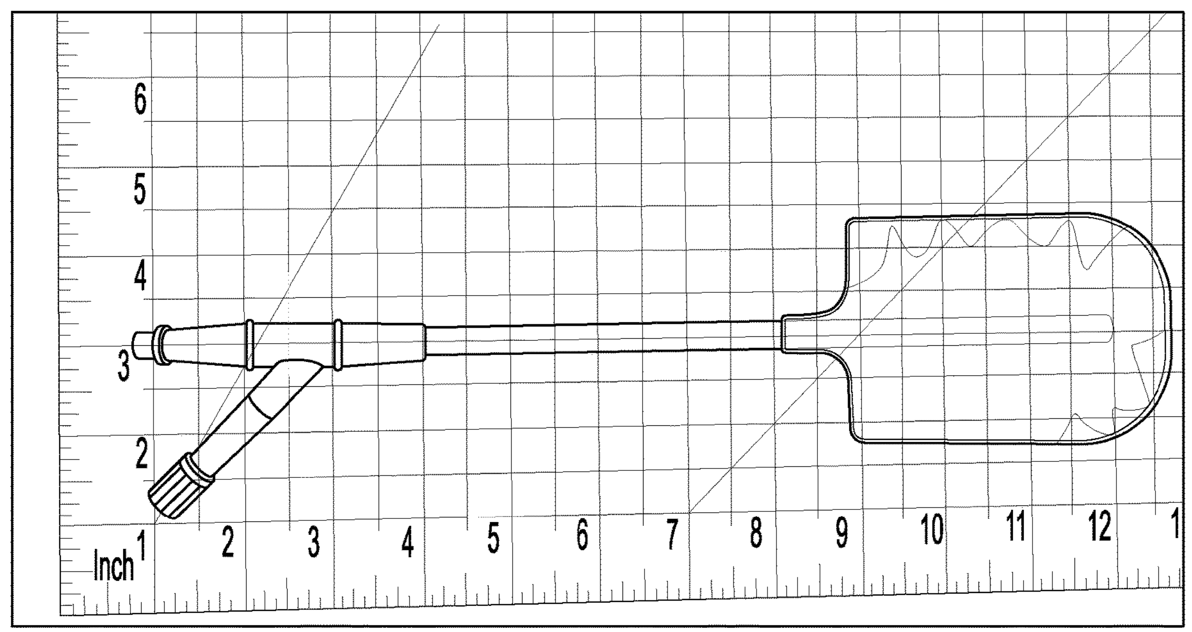
FIG. 13 shows another catheter device assembly, including Y connector hub, PTFE extrusion with cap, fill balloon, and UV adhesive, that may be used in the positioning device system of the invention.
Figure 14:
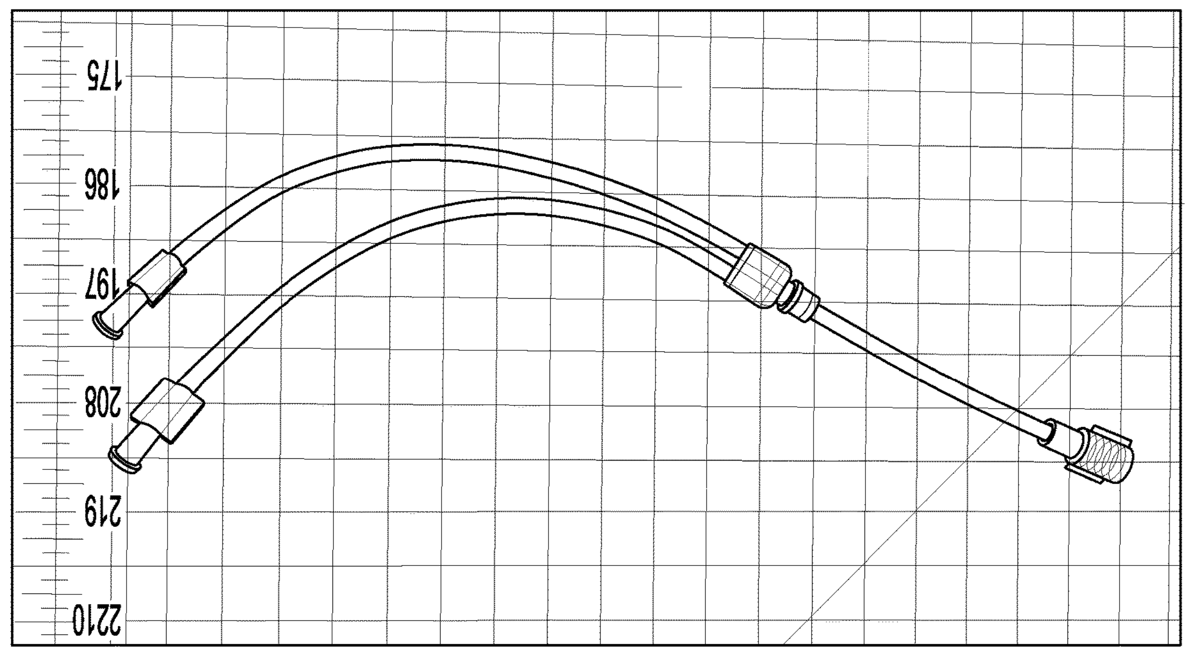
FIG. 14 shows another flexible Y-connector that may be used in the positioning device system of the invention.
Figure 15:
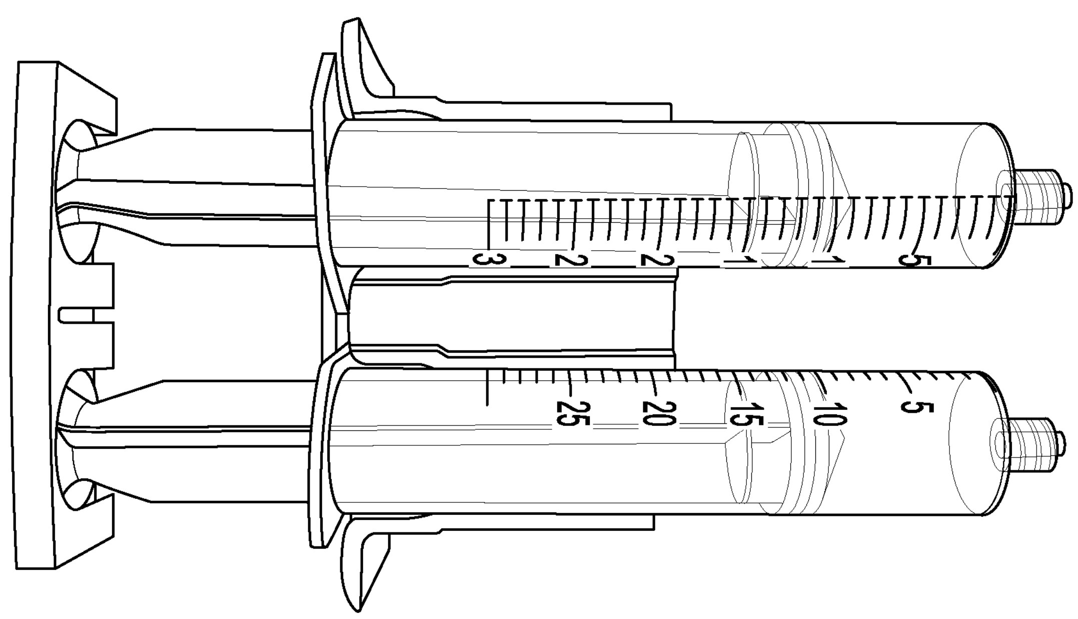
FIG. 15 shows an example of a dual syringe assembly with syringes that may be used in the positioning device system of the invention.
Figure 16:
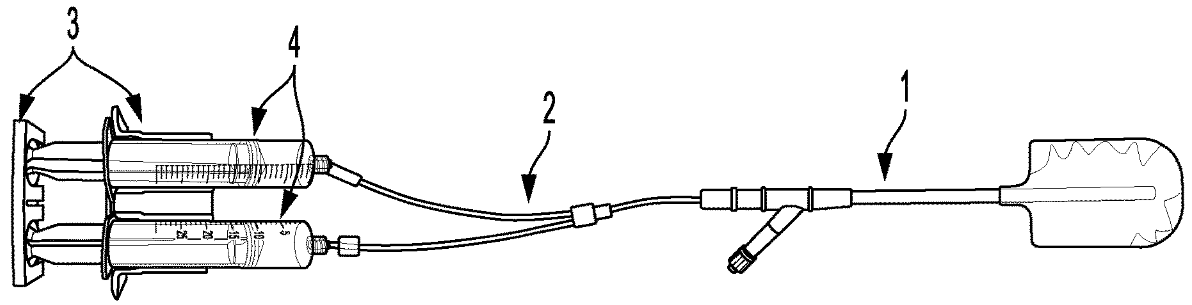
FIG. 16 shows an exemplary complete set-up of the positioning device system of the invention including 1) a catheter assembly, 2) a flexible Y connector, 3) a dual syringe assembly, and 4) syringes.
Figure 17:
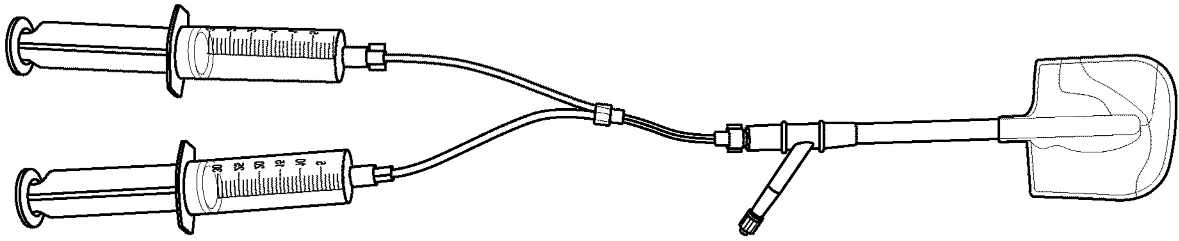
FIG. 17 shows another complete set-up of the positioning device system of the invention.
Figure 18A:
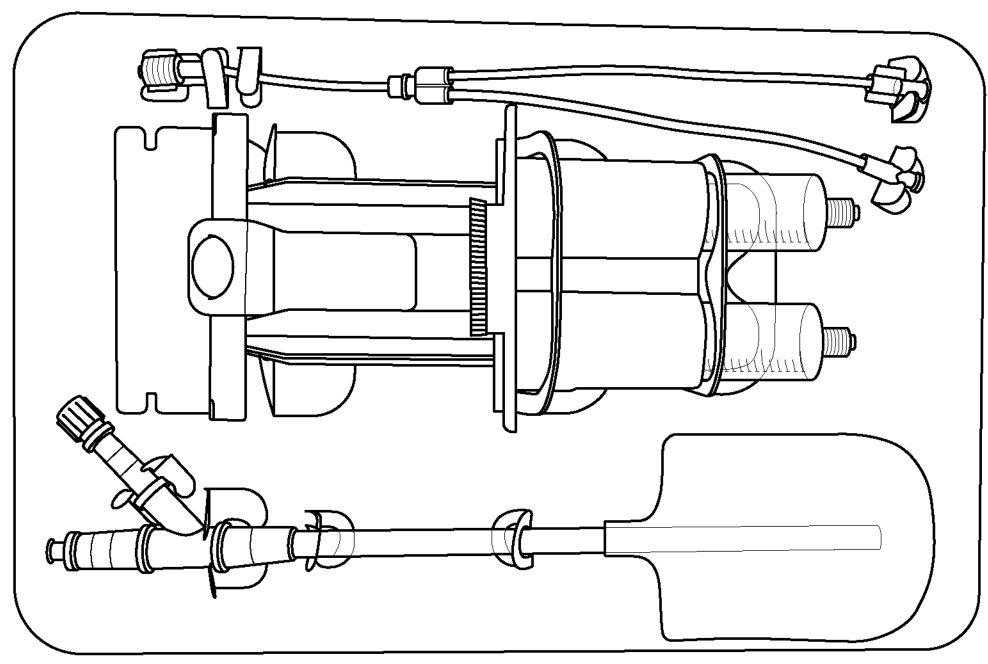
FIG. 18(*a*) and FIG. 18(*b*) show different examples of preloaded syringes (e.g., two syringes preloaded with 25 mL of hydrogel precursors each), a Y-connector, and a delivery system that features a container (e.g., an oversized reaction bag), each of which may be used in the positioning device system of the invention.
Figure 18B:
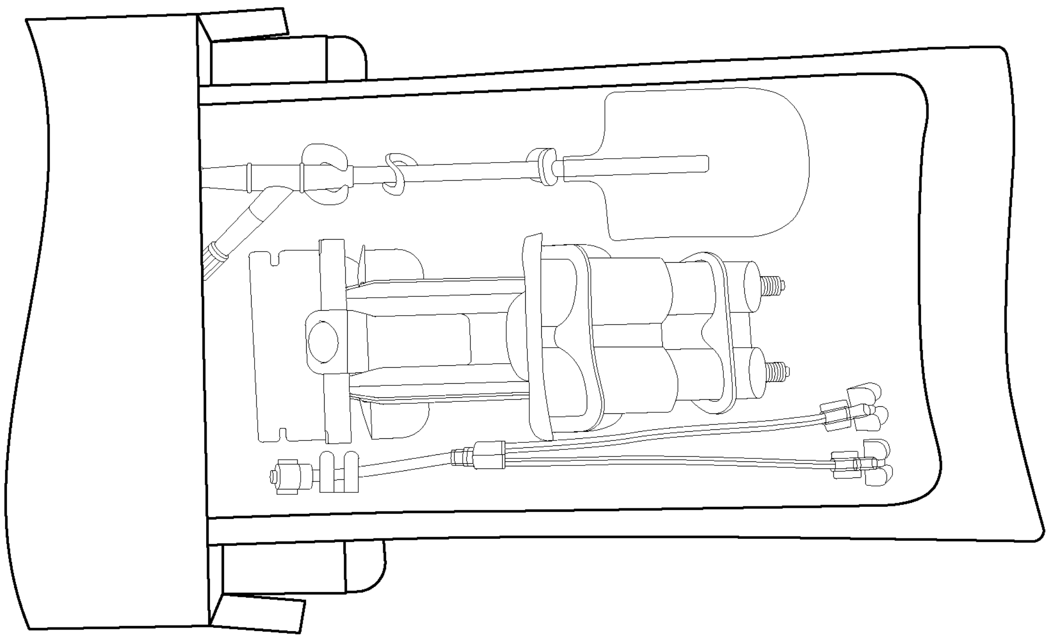

For example, the positioning device system of the invention may comprise a Y-connector, syringes, and a catheter device assembly. See FIG. 12. The catheter device assembly may comprise a stopcock, a saline flush port and plastic filament, a shaft, and a container (e.g., therapy bag, oversized reaction bag, fill balloon). See FIG. 12. The catheter device assembly may also comprise a Y-connector hub, a PTFE extrusion with a cap, a container (e.g., therapy bag, oversized reaction bag, fill balloon), and UV adhesive. See FIG. 13. Another example of a flexible Y-connector that may be used to connect the receptacle delivery device to the catheter device assembly is shown in FIG. 14. FIG. 15 shows an example of a dual syringe assembly with syringes that may contain the hydrogel precursor material and that may be used in the positioning device system. FIG. 16 shows an exemplary complete set-up of the positioning device system including 1) a catheter assembly, 2) a flexible Y connector, 3) a dual syringe assembly, and 4) syringes. FIG. 17 shows another complete set-up of the positioning device system. FIG. 18(*a*) and FIG. 18(*b*) show different examples of preloaded syringes (e.g., two syringes preloaded with 25 mL of hydrogel precursors each), a Y-connector, and a delivery system that features a container (e.g., therapy bag, oversized reaction bag, fill balloon), each of which may be used in the positioning device system of the invention.

Figures 19A, 19B, 19C, 19D, 19E, 19F, 19G, 19H, 19I:
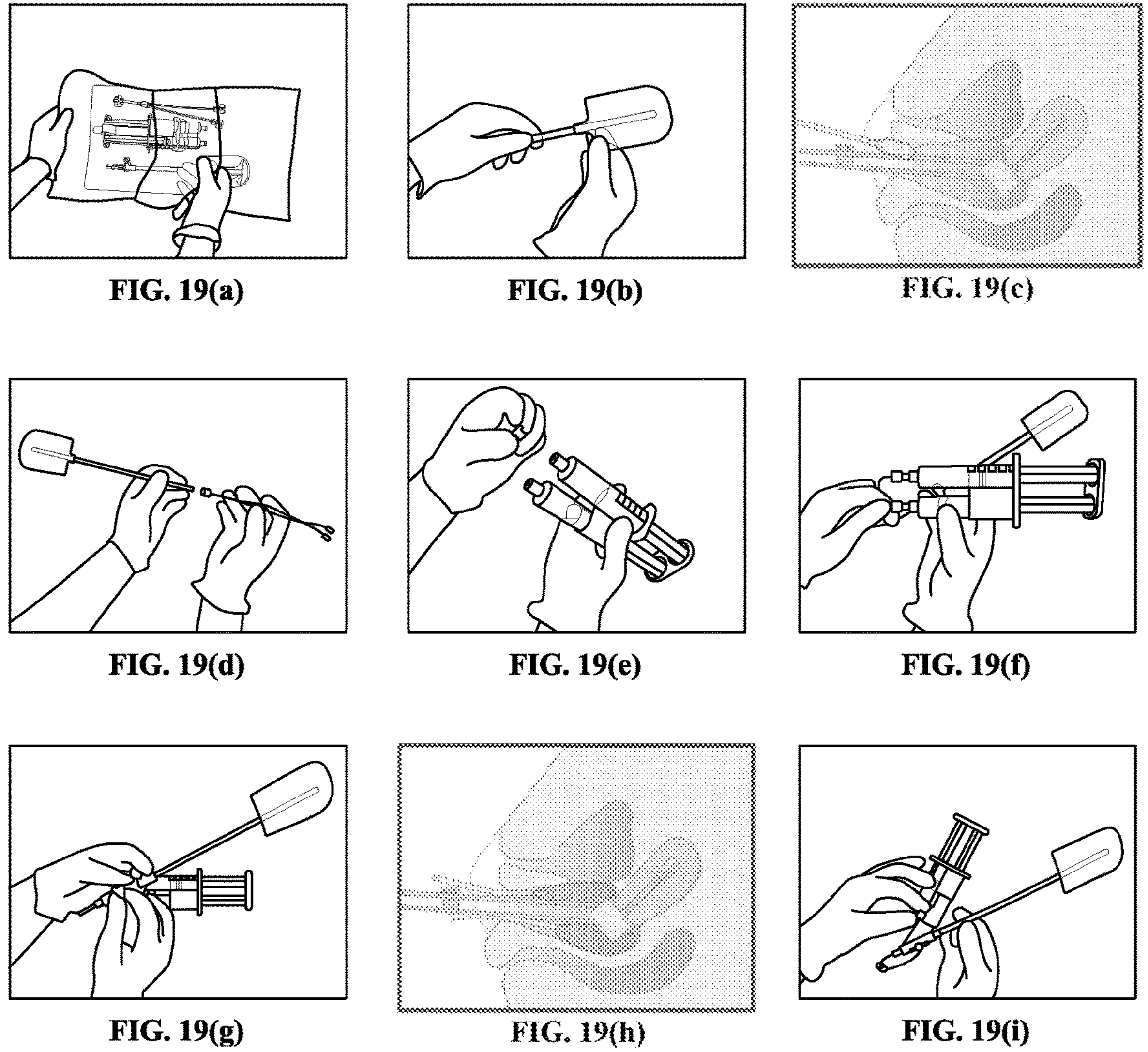
FIGS. 19(*a*), 19(*b*), 19(*c*), 19(*d*), 19(*e*), 19(*f*), 19(*g*), 19(*h*), and 19(*i*) show an example of the installation steps for the positioning device system of the invention.

The positioning device system of the invention may be installed in a patient by first, aseptically, opening the package containing the components of the positioning device system and removing them (FIG. 19(*a*)), holding the catheter device assembly by the shaft and lubricating the container as desired per facility protocol (FIG. 19(*b*)), gently inserting the catheter device assembly inside the body cavity to the desired depth anterior or posterior to the brachytherapy treatment applicator(s) (FIG. 19(*c*)), connecting the Y-connector tubing to the shaft of the catheter device assembly (FIG. 19(*d*)), removing the caps from each of the hydrogel syringes (FIG. 19(*e*)), connect the split ends of the Y-connector to each male luer connector on the hydrogel syringes (FIG. 19(*f*)), turning the stopcock on the catheter device assembly to the open position, infusing the contents from the syringes to desired fill volume (50 mL max), and turning the stopcock to the closed position (FIG. 19(*g*)), with the container (therapy bag, oversized reaction bag, fill balloon) filled and stopcock turned to the closed position, performing radiation treatment according to facility protocols (FIG. 19(*h*)), and removing the plastic filament on the saline port of the catheter device assembly, carefully removing the catheter device assembly from the patient, and disposing of the catheter device assembly per facility protocol (FIG. 19(*i*)).

Brachytherapy Applicator

Figure 2:
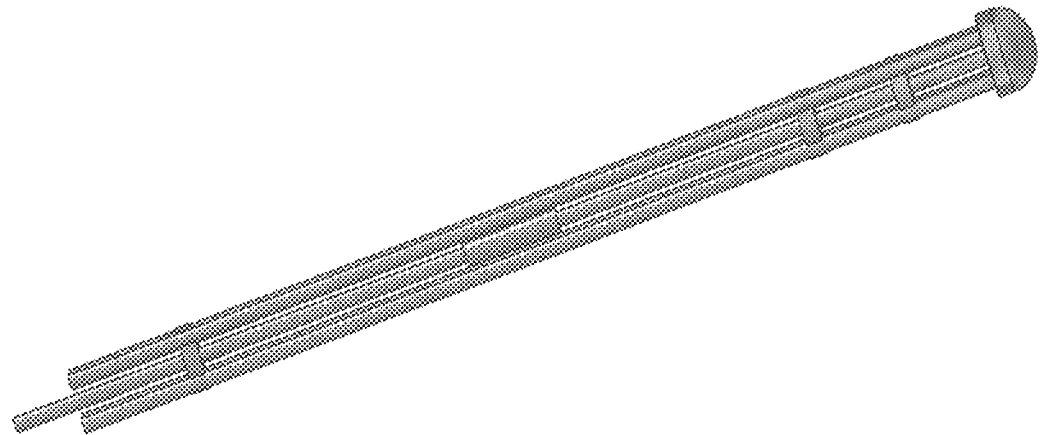
FIG. 2 shows a 3-D drawing of an exemplary brachytherapy applicator of the invention.

The invention also relates to a rigid, reusable, 5-channel scaffold (tandems with architectural support), fixed-geometry brachytherapy applicator for brachytherapy, including, for example, intracavitary vaginal/rectal high-dose-rate brachytherapy. The brachytherapy applicator of the invention can be used in conjunction with the thiol-Michael addition hydrogel and method thereof of the invention. For example, the thiol-Michael addition hydrogel of the invention can expand to fill the space among the channels and between the applicator and the vaginal mucosa. FIG. 2 shows a 3-D drawing of a preferred applicator of the invention, which may be used in conjunction with the thiol-Michael addition hydrogel and method thereof of the invention.

Preferably, the brachytherapy applicator of the invention has 1 central tandem and 4 tandems arranged in ring, equidistant from the central tandem; all the tandems are straight and rigid; the tips of the tandems are attached to the concave side of a dome that is slightly wider than the tandem array, and the tandem insertion is via embedding within the dome applicator tip, so that the outer surface in contact with the cranial aspect of the vagina or rectum is smooth; the array of tandems is connected via a scaffold structure, permitting geometric stability and architectural support while allowing for flow of polymeric gels, such as the inventive thiol-Michael addition hydrogel; each tandem is 300-350 mm in length and 2-4 mm in diameter with a central hollow channel for one or more brachytherapy sources, compliant with standard HDR afterloader designs; a sliding ring for introducing IV tubing; a size nozzle for delivery equipment of polymeric gels, such as the inventive thiol-Michael addition hydrogel; and all precursor materials within the intended treatment area are CT/MRI compatible.

The brachytherapy applicator of the invention provides a real-time approach, resulting in a higher level of efficiency and clinical feasibility than existing methods for vaginal mold brachytherapy, which require several steps to create a patients-specific mold by translating a vaginal impression to an alginate negative to an acrylic mold over a several-day process. See Khoury et al., *Brachytherapy* 2015, 14(1), 51-55; Nilsson et al., *Brachytherapy* 2015, 14(2), 267-272. In addition, the brachytherapy applicator of the invention provides a number of improved features, elements, and characteristics over the existing options, such as, but not limited to: fixed geometry of the channels permits use of template plans for efficient 3-D radiation treatment planning; use with the thiol-Michael addition hydrogel of the invention provides the ability to treat a range of vaginal diameters with a single size applicator; improved patient comfort through narrow diameter at vaginal introitus; reusable titanium design permits low per-treatment cost for multichannel applicator vaginal brachytherapy, since only per-fraction cost is a result of the hydrogel kit; a small number of applicators required per center, since there is a single size (in contrast to existing vaginal cylinders, which must be purchased in a range of sizes); and a design providing a docking station for hydrogel tubing to slide delivery system along a central channel into the vaginal space.

The brachytherapy applicator of the invention can improve upon existing options for vaginal cuff brachytherapy by providing a customized solution that conforms to patient anatomy and can offer more precise radiation delivery while maintaining an efficient workflow. Therefore, the thiol-Michael addition hydrogel, related method, and brachytherapy applicator of the invention can dramatically improve the care of women receiving tandem-based brachytherapy for cervical cancer as well as adjuvant brachytherapy after hysterectomy for uterine cancers. For example, the brachytherapy applicator of the invention may be used in any of the methods of the invention described herein.

The invention further provides a kit for the positioning device system of the invention comprising the at least one receptacle delivery device optionally containing the thiol-Michael addition hydrogel invention or at least one precursor material of the thiol-Michael addition hydrogel invention; the catheter device assembly; and the container (e.g., therapy bag, oversized reaction bag, fill balloon); and optionally instructions for administration/installation of the positioning device system. For example, the invention provides a positioning device system kit comprising: a first syringe comprising, consisting of, or consisting essentially of at least one precursor material of the thiol-Michael addition hydrogel of the invention; a second syringe comprising, consisting of, or consisting essentially of at least one precursor material of the thiol-Michael addition hydrogel of the invention; a catheter device assembly; an oversized reaction bag; and instructions for administration of the positioning device system. For example, a first syringe of the kit may comprise, consist of, or consist essentially of at least one Michael acceptor, such as, for example, an oligomeric polyethylene glycol diacrylate, and optionally at least one aqueous base (e.g., $NaHCO_3$), a second syringe of the kit may comprise, consist of, or consist essentially of at least one thiol compound, such as, for example, a multi-arm, thiol-terminated PEG oligomer, and optionally at least one aqueous base (e.g., $NaHCO_3$). The aqueous base may be in either or both of the first and second syringes, and/or it may be in a third syringe separate from the other precursor materials. Preferably, a positioning device system kit of the invention comprises a first syringe comprising, consisting of, or consisting essentially of $PEGDA_{250}$, $PEGDA_{575}$, and $PEGDA_{700}$, dissolved in $NaHCO_3$, a second syringe comprising, consisting of, or consisting essentially of THIOCURE ETTMP 1300, dissolved in $NaHCO_3$. A positioning device system kit of the invention comprising the precursor materials of the thiol-Michael addition hydrogel invention may also be associated with the brachytherapy applicator of the invention. While the positioning device system kit of the invention comprising the precursor materials of the thiol-Michael addition hydrogel are typically for single-use administration, the brachytherapy applicator may be reusable with new positioning device system kits of the invention containing the precursor materials to the hydrogels of the invention.

As used herein, the term "instructions" when used in the context of a kit includes a publication, a recording, a diagram, or any other medium of expression which can be used to communicate the usefulness of the kit for its designated use. The instructions can, for example, be affixed to or included within a container for the kit.

For ease of storage and administration, compatible precursor materials of the thiol-Michael addition hydrogel of the invention may be placed in one syringe, separated from other precursor materials of the thiol-Michael addition hydrogel. For example, the base may be placed in one or both of two syringes containing the thiol precursor material and the acrylate precursor material, respectively.

According to some kits of the invention, each precursor material of the thiol-Michael addition hydrogel of the invention is contained in a separate syringe. If necessary for stability purposes, the syringe(s) may be stored frozen and thawed before administration, e.g., by placing in a refrigerator one or two days before administration.

Any receptacle or applicator means capable of holding, storing, and/or applying at least one precursor material of a thiol-Michael addition hydrogel of the invention may be used as the receptable delivery device in the positioning device system and kits thereof. Such a receptacle or applicator means may be in any configuration known to a person skilled in the art, such as, but not limited to, a pouch, a syringe, an ampoule, a bottle, a jar, a vial, or a box. The receptacles or applicator means may be made of any material suitable for the precursor materials contained therein and additionally suitable for short and/or long term storage under any kind of temperature. Such materials include, by way of example, inorganic materials, such as Type I glass (including amber colored glass), ceramics, metals (e.g., aluminum, tin, and tin coated tubes), etc., and organic materials such as inert polymers including polyolefins e.g., high density polyethylene), fluorinated polyolefins, and the like. Suitable receptacles or applicator means include those that maintain the sterility and integrity of their contents, for example, by providing a barrier to moisture. The preferred receptacles or applicator means is also one which is compatible with any chosen method of sterilization, including, for example, irradiation. The suitable receptacles or applicator means may have an appropriate applicator means to dispense the precursor materials of the thiol-Michael addition hydrogel from the receptacle or applicator means to the container attached to the catheter device assembly. The receptacles or applicator means may be sealed as separate articles or are combined into a single article of manufacture having a barrier between the receptacles or applicator means. This barrier can either be removed or destroyed allowing mixing of the precursor materials of the thiol-Michael addition hydrogel of the invention in each of the receptacles or applicator means at the appropriate time. Such barriers include frangible or crushable barriers or envelopes.

The kit of the invention may be used for packing applications for intracavitary brachytherapy (e.g., pelvic brachytherapy) treatment.

The kit may also contain in one or more receptacles or applicator means any of the additional components described herein, including, for example, at least one additional active ingredient, such as, for example, a bactericidal disinfectant, a bactericidal antiseptic, a bactericidal antibiotic, an antibiotic, a retinoid, other antiseptic agents, or mixtures thereof, and/or at least one pharmaceutically acceptable excipient, filler, extender, binder, humectant, disintegrating agent, solution retarder, absorption accelerator, wetting agent, adsorbent, lubricant, buffering agent, carrier, diluent, adjuvant, emollient, emulsifier, wax, solubilizer, electrolyte, hydroxyacid, stabilizer, cationic polymer, film former, thickener, gelling agent, superfattening agent, refattening agent, antimicrobial active compound, biogenic active compound, astringent, deodorizing compound, antioxidant, moisturizer, solvent, colorant, pearlizing agent, fragrance, opacifier, silicone, or mixtures thereof. These additional components may be in the same or different receptacles or applicator means as the one or more receptacles or applicator means comprising the precursor materials of the thiol-Michael addition hydrogel.

It is to be understood that both the foregoing general description and the following detailed description are exemplary and explanatory only and are not restrictive of the invention claimed. As used herein, the use of the singular includes the plural unless specifically stated otherwise.

EXPERIMENTAL

In the following examples, efforts have been made to ensure accuracy with respect to numbers used, but some experimental error and deviation should be accounted for. The following examples are for illustrative purposes only and are not intended, nor should they be construed as limiting the invention in any manner. Those skilled in the art will appreciate that variations and modifications of the following examples can be made without exceeding the spirit or scope of the invention.

Materials and Methods

THIOCURE ETTMP 1300 (THIOCURE®) was generously donated by Bruno Bock Thiochemicals and used as received. Poly(ethylene glycol) diacrylate (PEGDA) was purchased from Sigma Aldrich and used as received. The $M_n$ of PEGDA was determined by $^1H$ NMR spectroscopy prior to use. Molecular weights of PEGDA were determined to be 261, 513, and 668 g/mol. $NaHCO_3$ was purchased from Sigma Aldrich and used as received. Rheological experiments were performed on a DHR 2 parallel-plate rheometer using 25 mm disposable aluminum plates with a gap of 1 mm. Specific gravity was determined using a specific gravity kit purchased from Mineralab and an electronic balance. Cells were purchased from ATCC. Media and supplements were purchased from Life Technologies.

Rheological Experiments

All rheological experiments were performed on a TA DHR-2 rheometer using 25 mm disposable Al plates at room temperature, repeated in triplicate, and conducted over a short time period to ensure consistency. In a representative procedure, THIOCURE was weighed into a 6 dram vial (389 mg, 0.30 mmol, 0.90 mmol thiol), dissolved in 0.1 M $NaHCO_3$ (0.69 mL, ~50 wt % total), and agitated with a vortex mixer to dissolve. PEGDA (300 mg, 0.45 mmol, 0.9 mmol acrylate) was measured into a syringe and injected into the THIOCURE solution. The solution was mixed by manual agitation and rapidly placed between two 25 mm parallel plates in the rheometer. The gap was lowered to 1 mm and excess material was trimmed. Applying a constant normal force of 0.15±0.1 N minimized plate slippage. In cases where the hydrogel formed very slowly, the normal force was adjusted to 0.1±0.1 N to prevent slowly-gelling material displacement. Hydrogel formation was monitored for 1 h (1 Hz, 0.3% strain) followed immediately by a frequency sweep (0.1 to 100 Hz, 0.3% strain, 10 points/decade). The gel point was defined as the crossover point between G' and G" (usually before data collection began). The time to 10 kPa was measured as the first time point with a G' modulus above 10 kPa. The time to plateau was estimated as the first data point in the plateau region during the time sweep. An additional 90 s were added to each recorded time point to account for the time required to mix the solution, load the plates, and begin the test. Equilibrium shear-modulus was taken from the low-frequency G' value during the frequency sweep. After completion of the test, the hydrogels were removed from the rheometer and a portion was weighed ($m_{gel}$). The hydrogels were dried in vacuo at approximately 80° C. for 24 h. At this point, the hydrogels were weighed ($m_{dry}$) again to determine the initial water content using the following equation:

$$\text{wt \% water} = \frac{m_{gel} - m_{dry}}{m_{gel}} \times 100$$

The gel fractions of each sample were determined by immersing the dried hydrogel (approx. 100 mg samples) in 50 mL of dichloromethane followed by sonication for 90 min. The solvent was replaced and the hydrogel sonicated for an additional 90 min. Drying in vacuo overnight followed by weighing ($m_{extracted}$) led to determination of the gel fraction using the following equation:

$$\text{Gel Fraction} = \frac{m_{extracted}}{m_{dry}} \times 100$$

Synthesis of Hydrogels for Water Absorption Studies

Unless specified, all samples were prepared with 1:1 thiol:acrylate stoichiometry and with 50 wt % water content and a 0.1 M $NaHCO_3$ solution. In a representative procedure, THIOCURE-ETTMP 1300 (389 mg, 0.89 mmol thiol) was weighed into a 6-dram vial and dissolved in 0.1 M $NaHCO_3$ (0.69 mL, ~50 wt %). In a separate, tared syringe, $PEGDA_{668}$ ($M_n$=668 g/mol, 300 mg, 0.89 mmol acrylate) was measured and quickly added to the THIOCURE solution. The solution was swirled to mix and allowed to sit for 1 h. After gelation was confirmed using an inversion test, in which no flow occurs after inversion of the vial for 1 min, the hydrogels were removed from the vial and weighed followed by drying the intact hydrogel in vacuo at ~80° C. for 24 h. Gel fractions were determined using similar methods, but a sohxlet extractor was used instead of a solvent bath to remove extractables.

Swelling studies were performed as follows: Three small pieces (~20 mg) of a dried hydrogel sample were cut using a razor blade and weighed. The hydrogel pieces were immersed in vials containing approximately 3 g reverse-osmosis water which had been pre-equilibrated for 15 min in a 37° C. water bath. In 10 min intervals over the course of an hour, the hydrogels were rapidly removed, patted dry with a paper towel, weighed, and returned to the water bath. After 1 h, the hydrogels were allowed to equilibrate at 37° C. for 2 d and weighed a final time to determine the equilibrium water absorption.

Swelling Studies on Undried, As-Formed Hydrogels

Unless specified, all samples were prepared with 1:1 thiol:acrylate stoichiometry and with 50 wt % water content and a 0.1 M $NaHCO_3$ solution. Hydrogels were made in a 6-dram vial using the above-described procedure. The hydrogels were allowed to sit for 20 min and removed from the vial. Three 50-100 mg pieces were cut from the hydrogel. The pieces were immersed in vials containing approximately 5 mL of water pre-equilibrated at 37° C. The vials were returned to a water bath set to 37° C. The vials were removed in 10 min intervals, quickly weighed, and returned to the water bath. Measurements were taken for 1 h. Water uptake was calculated as before. Specific gravity was determined using a specific gravity kit and balance. The hydrogels were weighed on a balance in air ($m_{air}$). The hydrogels were then suspended underwater in the basket provided in the kit and weighed again ($m_{wet}$). The specific gravity could be calculated using the following equation:

$$\text{Specifc Gravity} = \frac{m_{air}}{m_{wet} - m_{air}}$$

The specific gravity of the hydrogels at the beginning of the swelling was determined on a separate piece cut from the same hydrogel precursor. At the end of 1 h, the specific gravity of the swollen hydrogels was determined for each piece, and the average value taken as the specific gravity for the swollen hydrogels. Under the assumption that the density of water at room temperature is ~1 g/mL, the specific gravity was taken to be the density. Measuring the density allowed for volume determination of the irregularly shaped pieces.

Swelling studies on the as-formed, undried hydrogels were also performed under 10 kPa normal force to demonstrate their ability to displace vaginal tissue. The PEGDA and aqueous $NaHCO_3$ were weighed into a 6-dram vial as before. The THIOCURE was added using a syringe and the contents were mixed and immediately poured into a Teflon mold. The solution was covered with a piece of silicone-coated Mylar and a glass plate and allowed to gel for 30 min. At this time, the hydrogel was removed from the mold and a square (~1.5 cm×1.5 cm) was cut. The exact dimensions were measured and the gel was placed in a DHR-2 rheometer fit with a concentric cylinder lower geometry. An upper parallel-plate geometry was lowered to the hydrogel. The normal force was adjusted to exert a constant 10 kPa of force (calculated based on the area of the hydrogel). The cylinder geometry was filled with 20 mL of deionized water preheated to 37° C. and the temperature of the lower geometry was set for 37° C. The gel was allowed to swell for 24 h and the change in gap necessary to maintain 10 kPa normal force was measured.

Imaging Studies

Samples were imaged on a SOMATOM sliding gantry CT unit (Siemens Healthcare, Erlangen, Germany) with an 80 cm bore, located at the University of Virginia Cancer Center. In a representative procedure, THIOCURE (5.72 g, 1:1 thiol:acrylate) was weighed into a 50 mL centrifuge tube and dissolved in 10.7 mL of 0.25 M $NaHCO_3$. $PEGDA_{668}$ was weighed into a tared syringe. The $PEGDA_{668}$ was rapidly added into the THIOCURE solution. The solution was rapidly mixed and the titanium applicator was placed in the tube. The hydrogel was allowed to form for 10 min. The tube was placed in a water bath and the hydrogel was imaged. A slice thickness of 3 mm, 120 kVP was used. Images were reconstructed using the standard filtered back projection algorithm on the scanner system. Images were processed using Brachyvision 13.0 brachytherapy treatment planning software (Varian Medical Systems, Palo Alto, CA).

Statistical Analysis

Statistical testing was performed using JMP software. First an analysis of variance (ANOVA) was performed followed by a Tukey's HSD with confidence interval $\alpha$=0.05.

Hydrogel Synthesis for Biological Studies

THIOCURE ETTMP 1300 was dissolved in 0.25 M $NaHCO_3$ at a concentration of 340 mg/mL. The solution was sterile filtered inside a biosafety cabinet. The solution (1.14 mL) was pipetted into a well on a 12 well plate. To the solution was added 0.27 ml of $PEGDA_{758}$ which had also been sterilized through filtration through a 0.27 μm PDFE filter. The solutions were stirred with a pipette tip to mix, covered, and allowed to sit for 1 h at which time the sample was removed for study.

Cell Maintenance

VK2/E6E7 human vaginal epithelial cells were purchased from ATCC and used upon arrival. Cells were cultured at 37° C. and 5% $CO_2$ with Keratinocyte-serum Free medium (Gibco) supplemented with 0.1 mg/mL human recombinant epithelial growth factor and 0.05 mg/mL bovine pituitary extract (Gibco). Cells were cultured in a T-75 flask and subcultured when ~80% confluent. Cells were washed with phosphate buffered saline and incubated with 0.25 Trypsin-EDTA for 7 min to suspend. A 1:2 subculturing ratio was used.

Cell Seeding

Following suspension, trypsin was neutralized with Dulbecco's modified eagle medium, F-12 complete with 10% fetal bovine serum. Cells were then centrifuged for 10 min at 4° C. at 120 g. Vaginal epithelial cells were then counted using a hemocytometer. 25,000 cells/well were seeded into a 24 well plate and allowed to attach and proliferate for 24 h before experimentation. Pre-formed sterile hydrogels were cut into pieces and placed into wells containing cells with fresh media. Cytotoxicity experiments were performed after 24 h incubation and ELISA samples isolated after 48 h incubation.

Cytotoxicity Assay

A Cell Titer Glo assay was used to measure cell viability and followed manufacturer's protocols. Following incubation, hydrogels were removed and fresh media (0.25 mL) was added to each well. After allowing the samples to come to room temperature, equal volume of Cell Titer Glo reagent was added to each well and incubated for 10 min. Each sample was subsampled 3 times into a 96-well plate and read on a SpectraMax M2 plate reader in luminescence mode. Cell viability is calculated as compared to untreated control cells on the same plate.

ELISA Assay

An ELISA assay sensitive to IL-8 was performed according to manufacturer's protocol. Briefly, cell media was isolated after 48 h of hydrogel incubation and kept at 4° C. until use. All ELISA reagents and samples were brought to room temperature before use. Control, hydrogel, and IL-8 standards were incubated for 1 h at room temperature in the ELISA plate coated with IL-8 antibody. After vigorous washing 3 times with wash buffer, anti-IL-8-biotin was added to each well and incubated for 1 h. Following 3 additional vigorous washes, streptavidin-HRP solution was made and introduced to wells for a 30 min incubation. A final 3 washes yielded HRP-active samples. HRP solution was added to each well and incubated for 30 min in the dark. Stop solution was added immediately after 30 min and the plate read for absorbance at 550 nm and 450 nm using a SpectraMax M2 plate reader. The IL-8 standards were used to make a linear relationship between absorbance and IL-8 concentration, which was then used to calculate the concentration of IL-8 in control and hydrogel samples.

Statistical Testing

Statistical testing was performed using IMP software. First an analysis of variance (ANOVA) was performed to compare control cells to cells exposed to hydrogels followed by a student's t-test with confidence interval $\alpha$=0.05.

EXPERIMENTAL RESULTS

Table 1 summarizes the data for rheological experiments. Gel fractions typically exceeded 90%, indicating high conversion of starting materials. In almost all cases, the gel point occurred before data collection began (<90 s). Hydrogels from $PEGDA_{261}$ gelled more slowly than other compositions, with the gel time occurring after approximately 2 min. The hydrogel sample with lower initial water content (25 wt %) required higher base concentration for gelation to occur. Despite the higher base concentration, the gel time still exceeded 90 s.

TABLE 1

Hydrogel formation times and modulus data for hydrogel compositions

| PEGDA MW (thiol:acrylate) | [$NaHCO_3$] (M) | Gel Time (min) | Time to 10 kPa (min) | Time to Plateau (min) | G' (kPa) | Gel Fraction (%) |
|---|---|---|---|---|---|---|
| 261 (1:1) | 0.1 | 2.1 ± 0.3 | 8.6 ± 1.4 | 29.3 ± 6.2 | 65.8 ± 35.4 | 94.1 ± 4.4 |
| 261 (1.2:1) | 0.1 | 2.1 ± 0.1 | 7.9 ± 2.1 | 38.3 ± 10.4 | 94.6 ± 57.1 | 97.2 ± 3.8 |
| 513 (1:1) | 0.1 | <1.5 | 5.4 ± 1.1 | 12.9 ± 1.2 | 23.8 ± 1.8 | 82.3 ± 3.0 |
| 513 (1.2:1) | 0.1 | <1.5 | 4.1 ± 1.1 | 12.8 ± 3.3 | 45.7 ± 16.9 | 94.5 ± 0.3 |
| 668 (1:1) | 0.1 | <1.5 | 4.7 ± 0.3 | 15 ± 0.3 | 41.3 ± 5.5 | 96.5 ± 0.6 |
| 668 (1.2:1) | 0.1 | <1.5 | 4.5 ± 0.4 | 14.5 ± 1.6 | 37.6 ± 18.8 | 96.3 ± 0.9 |
| 668 (1:1) | 0.175 | <1.5 | 3.0 ± 0.7 | 8.9 ± 3.2 | 43.8 ± 11.2 | 83.6 ± 5.7 |
| 668 (1:1) | 0.25 | <1.5 | 1.8 ± 0.2 | 6.4 ± 1.2 | 33.6 ± 6.6 | 93.3 ± 1.7 |

TABLE 1-continued

Hydrogel formation times and modulus data for hydrogel compositions

| PEGDA MW (thiol:acrylate) | [$NaHCO_3$] (M) | Gel Time (min) | Time to 10 kPa (min) | Time to Plateau (min) | G' (kPa) | Gel Fraction (%) |
|---|---|---|---|---|---|---|
| 668 (1:1) | 0.25* | 2.0 ± 0.2 | 6.0 ± 1.2 | 20.7 ± 4.9 | 119.1 ± 13.2 | 95.9 ± 0.9 |
| 668 (1:1) | 0.1[‖] | <1.5 | 3.2 ± 1.5 | 4.9 ± 2.2 | 9.1 ± 6.2° | 92.5[Δ] |

*25 wt % water,

‖75 wt % water;

°Modulus declined over 1 h from value >10 kPa,

ΔDried hydrogels too fragile to determine gel-fraction. Gel fraction determined from a separate sample formed in a vial (larger scale).

Figure 3A:
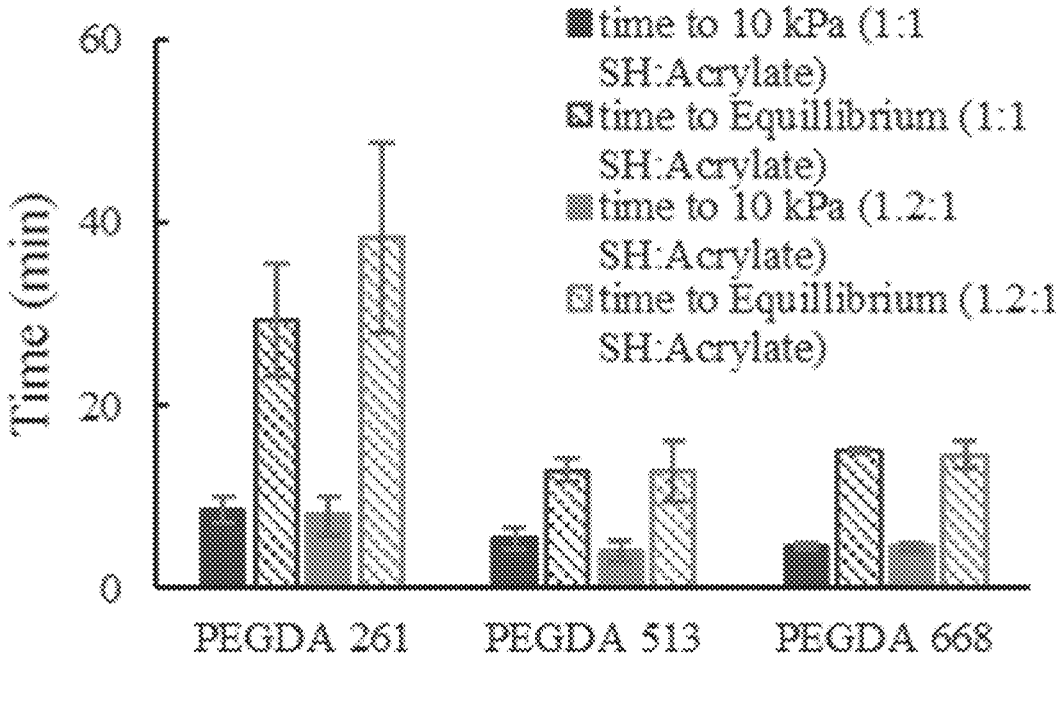
FIG. 3(*a*) shows the effect of PEGDA molecular weight on the gel-formation rate for exemplary hydrogels of the invention.
Figure 3B:
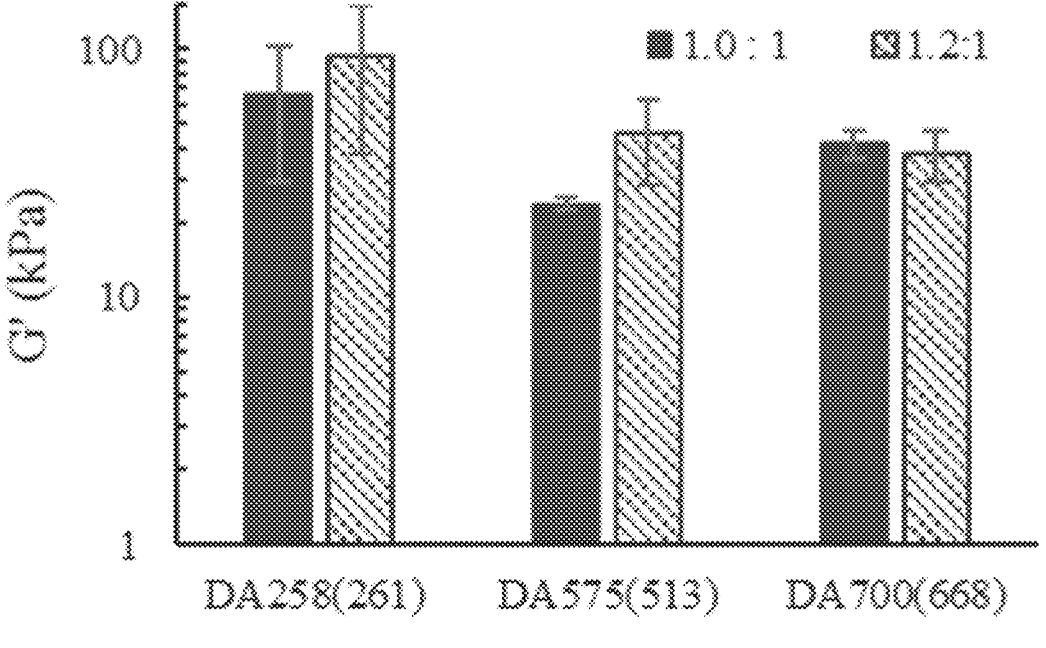

All hydrogels reached a storage modulus value of 10 kPa within 10 min (FIG. 3(*a*)), however, reagent stoichiometric ratios and PEGDA molecular weight minimally affected other observed properties. The time to the equilibrium storage modulus for hydrogels made from $PEGDA_{261}$ occurred within 30 to 40 min, which agreed with the previously observed slower gel formation. Hydrogels from longer PEGDA oligomers reached a plateau within 15 min with no statistical difference between $PEGDA_{513}$ and $PEGDA_{668}$. Reagent stoichiometry displayed negligible effect on the time to equilibrium storage modulus. All hydrogels possessed moduli between 20 and 100 kPa, well above the 10 kPa limit (FIG. 3(*b*)). PEGDA molecular weight exerted no statistically significant difference in the equilibrium storage modulus value.

Figure 4A:
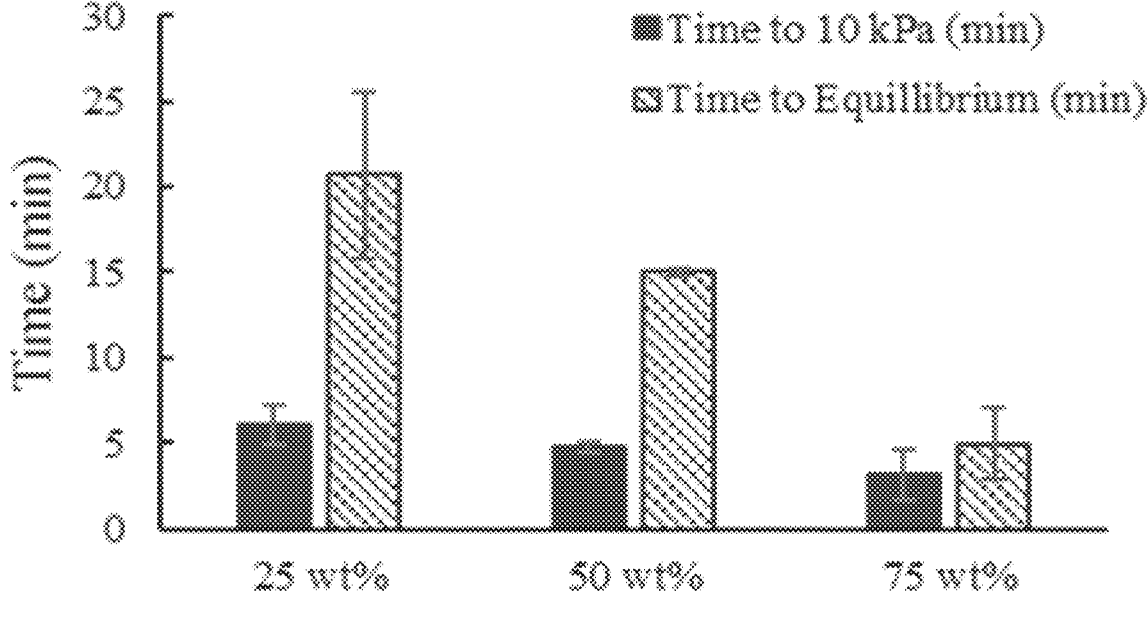
FIG. 4(*a*) shows the effect of initial water content on the gel-formation rate for exemplary hydrogels of the invention.
Figure 4B:
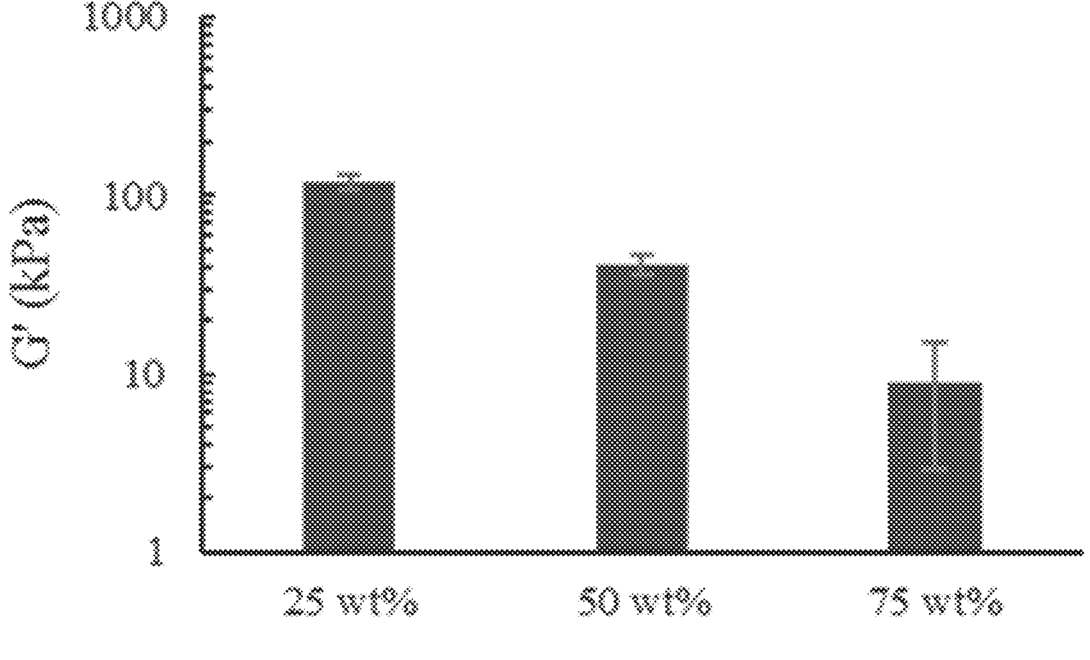

Changing the initial water content exerted little effect on the time required to reach a 10 kPa modulus value (FIG. 4(*a*)) despite a longer observed gel time. Samples with 75 wt % water reached 10 kPa rapidly, though the modulus eventually declined to below 10 kPa as the hydrogel relaxed after formation. Water evaporation at long experimental times for this high water content sample could also potentially cause the modulus decrease. The intermediate 50 w % composition showed a time to 10 kPa statistically indistinguishable from the other two compositions with both following similar trends in the time required to reach an equilibrium modulus value. The 25 wt % water sample required over 20 min to reach a plateau, while hydrogels with 75 wt % water reached the equilibrium plateau in under 5 min. The initial water content exerted significant influence on the equilibrium modulus (FIG. 4(*b*)). Decreasing initial water content to 25 wt % water increased the modulus above 100 kPa while 75 wt % water led to an equilibrium modulus slightly below the required 10 kPa threshold.

Figure 5A:
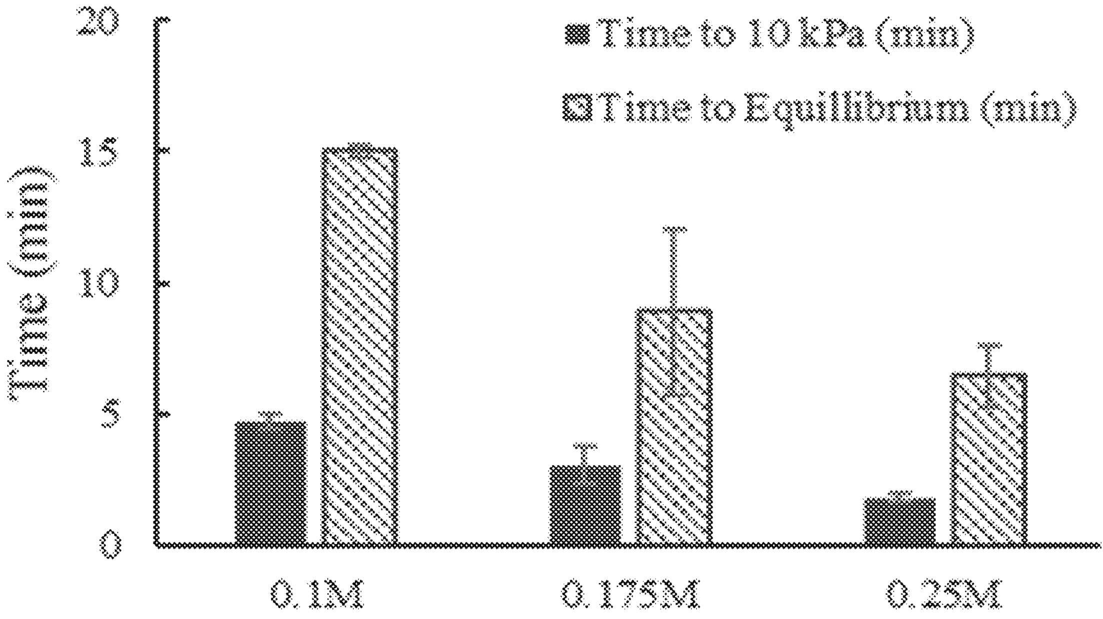
FIG. 5(*a*) shows the effect of base solution concentration on the gel-formation rate for exemplary hydrogels of the invention.
Figure 5B:
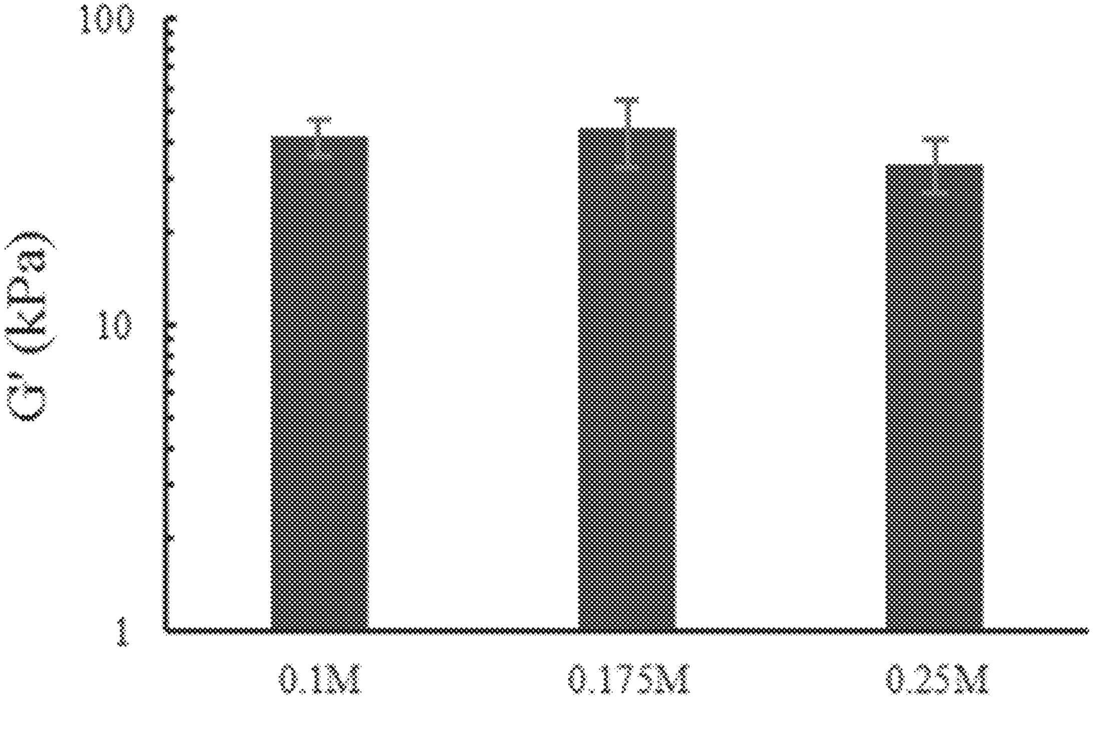

Increasing the base concentration to 0.175 M decreased the time to 10 kPa from 4.7 to 3.0 min, with the equilibrium modulus occurring after approximately 9 min (FIG. 5(*a*)). Higher base concentration (0.175 and 0.25M) resulted in hydrogels which reached a modulus of 10 kPa in under 2 min, with equilibrium occurring after 6 min. This represents an ideal time-frame for clinical application. Changing the catalyst concentration negligibly affected the equilibrium modulus (FIG. 5(*b*)).

Water Absorption

Figure 6A:
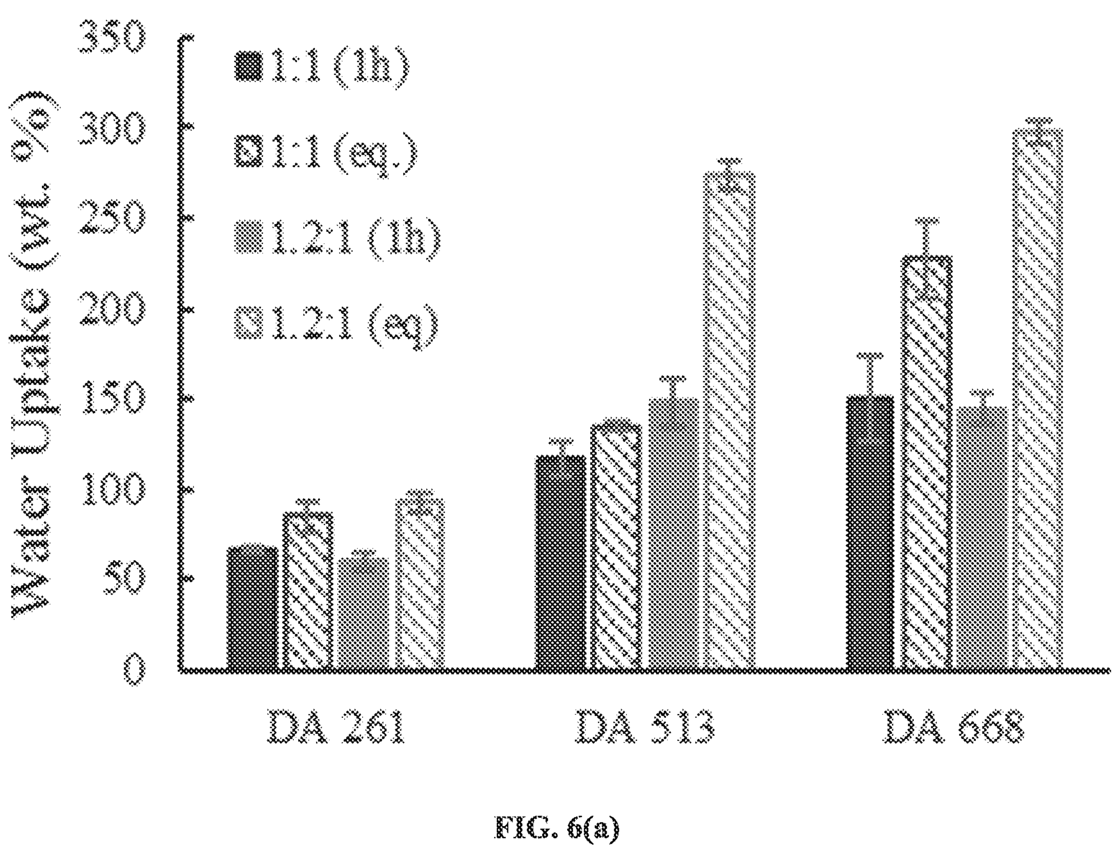
FIG. 6(*a*) shows the effect of PEGDA molecular weight on the water uptake of dried, extracted exemplary hydrogels of the invention.
Figure 6B:
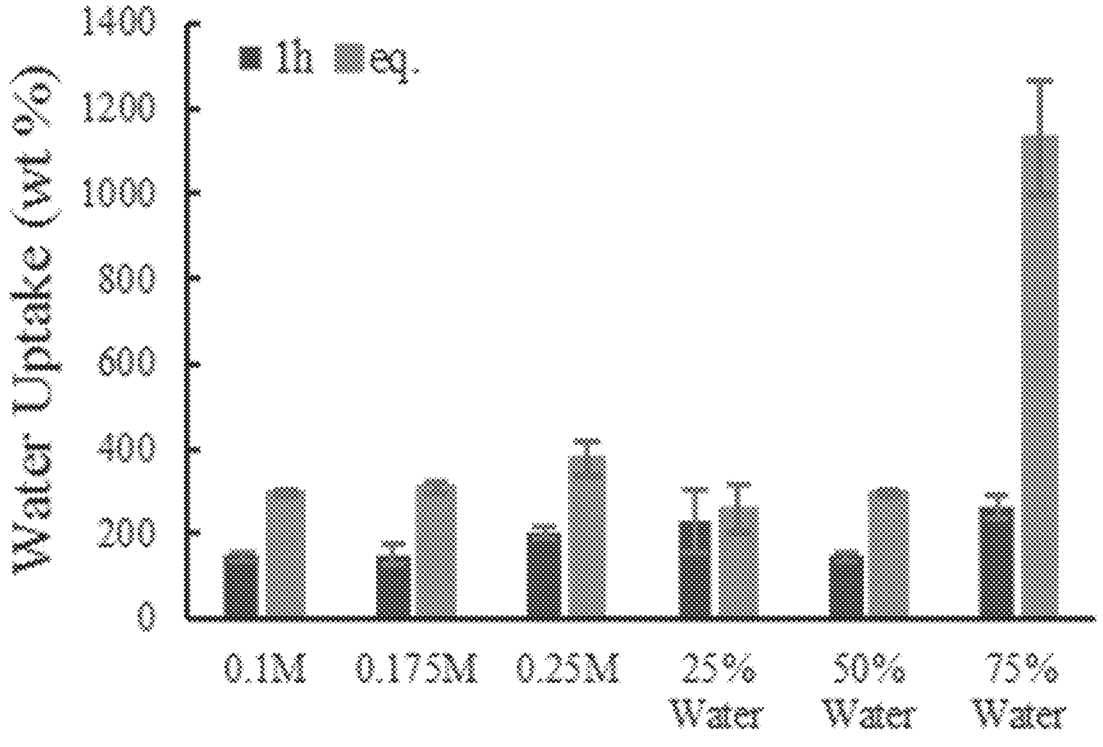
Figure 6C:
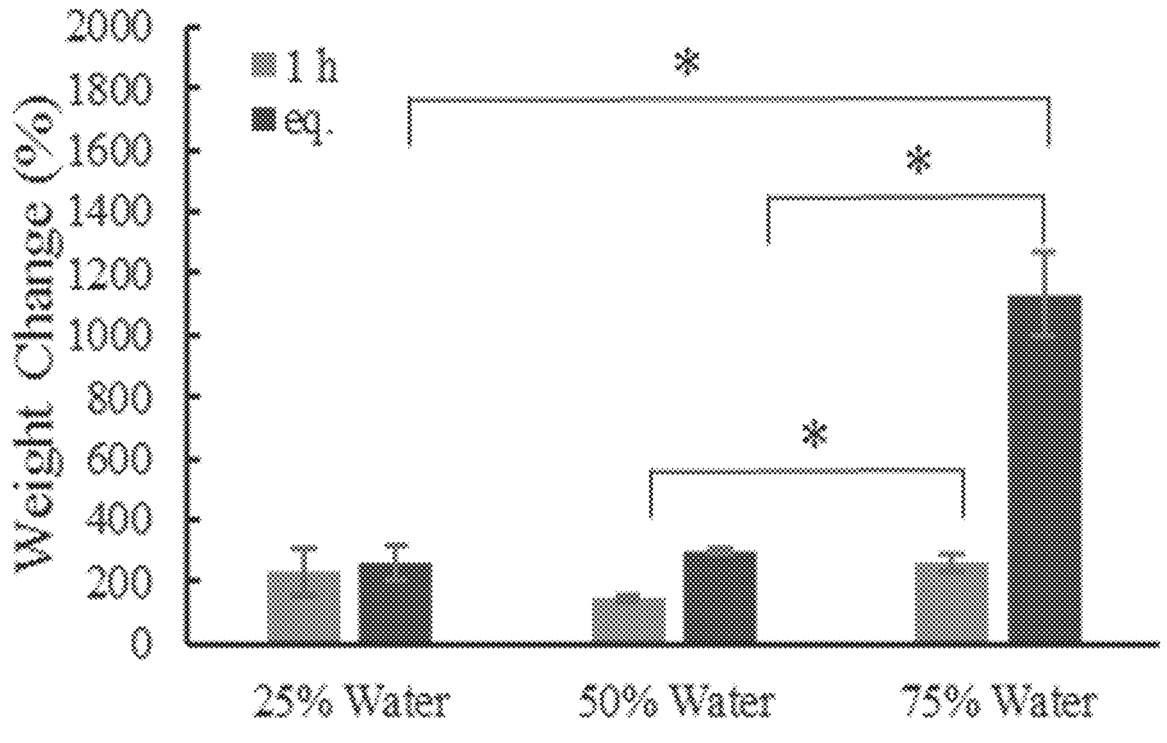

Longer PEGDA segments increased water absorption after both 1 h and at equilibrium (FIG. 6(*a*)). $PEGDA_{668}$ samples absorbed approximately 150 wt % water from the dry, extracted state in 1 h, with the equilibrium water absorption reaching between 250 and 300 wt % increase. Altering the thiol:acrylate stoichiometric ratio from 1:1 to 1.2:1 showed no effect on the short-term water absorption, although the samples with higher thiol content absorbed more water at equilibrium. Hydrogels from $PEGDA_{513}$ showed slightly lower but statistically insignificant short-term absorption while hydrogels from $PEGDA_{261}$ absorbed markedly less water. Hydrogels from $PEGDA_{261}$ absorbed less than 100 wt % water even at equilibrium.

Increasing the $NaHCO_3$ concentration used to form the hydrogels increased water absorption (FIG. 6(*b*)). Compositions made with 0.175 M $NaHCO_3$ absorbed 150 wt % water in 1 h and reached an equilibrium absorption slightly above 300 wt % increase, although this result did not vary from hydrogels made using 0.1 M $NaHCO_3$ to a statistically significant extent. Using 0.25 M $NaHCO_3$ resulted in hydrogels that absorbed almost 200 wt % water after 1 h and absorbed almost 400 wt % at equilibrium, a significant increase over other samples. Changing the initial water content (FIG. 6(*c*)) did not significantly affect the water absorption with the exception of the hydrogel made with 75 wt % water, which absorbed almost 1200% at equilibrium.

Figure 7A:
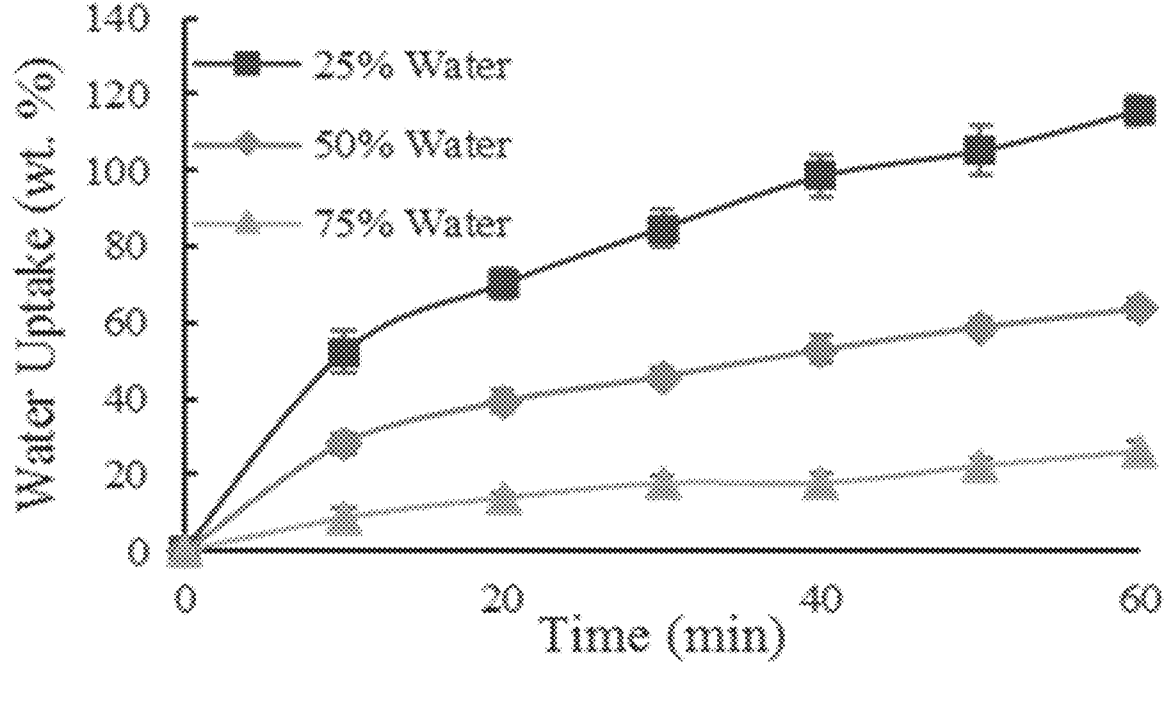
FIG. 7(*a*) shows the short-term water uptake for undried, unextracted exemplary hydrogels of the invention with differing initial water content.
Figure 7B:
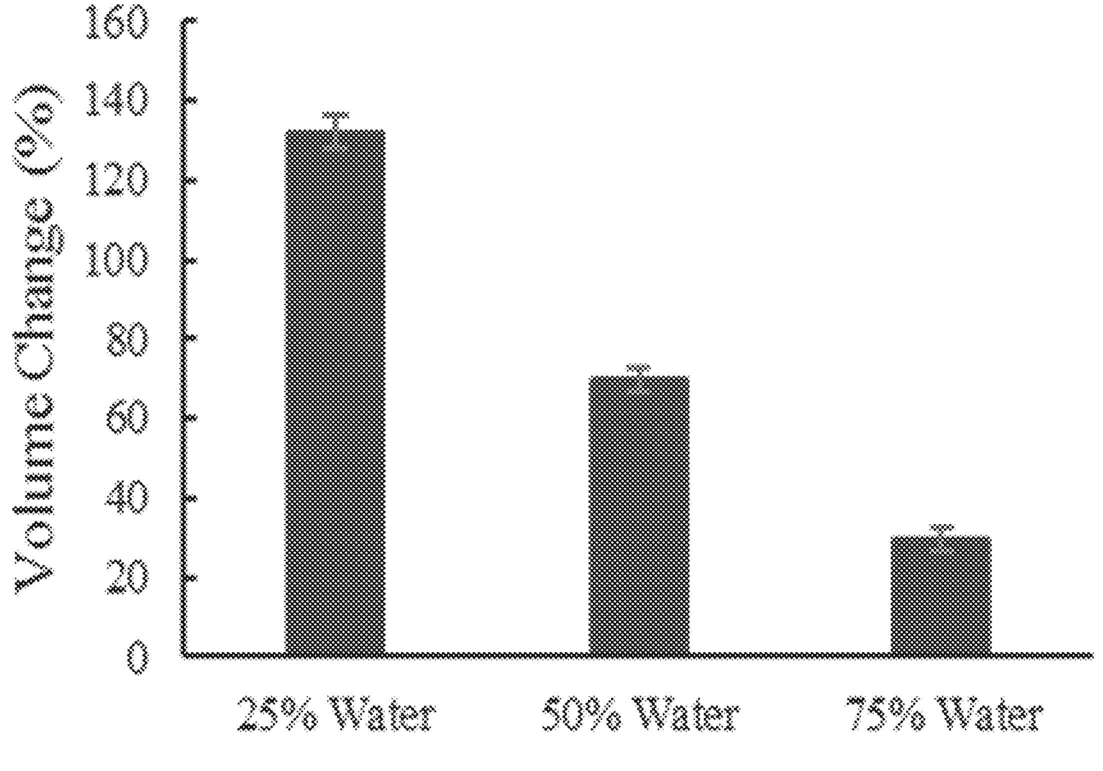

Studying water absorption in the as-formed (undried, unextracted) state provided important information, as the hydrogels will eventually be swollen in vivo without prior drying or extraction. Measuring the specific gravity of the pieces before and after the experiment allowed for observation of volume change instead of mass change. As the undried, unextracted samples most closely resembled the state of the hydrogels in clinical settings, observing volume change was especially important in this experiment. Increasing the initial water content led to a decrease in water absorption (FIG. 7(*a*)). Even in the undried state, hydrogels absorbed up to an additional 40 wt % in 1 h. Measuring the hydrogel density in the dried state and after swelling allowed for characterization of the volume change in addition to the mass change (FIG. 7(*b*)). As expected, hydrogels with lower initial water content displayed a greater volume increase over the course of 1 h; the hydrogel containing 25 wt % water increased volume up to 132 vol % in 1 h.

Figure 8:
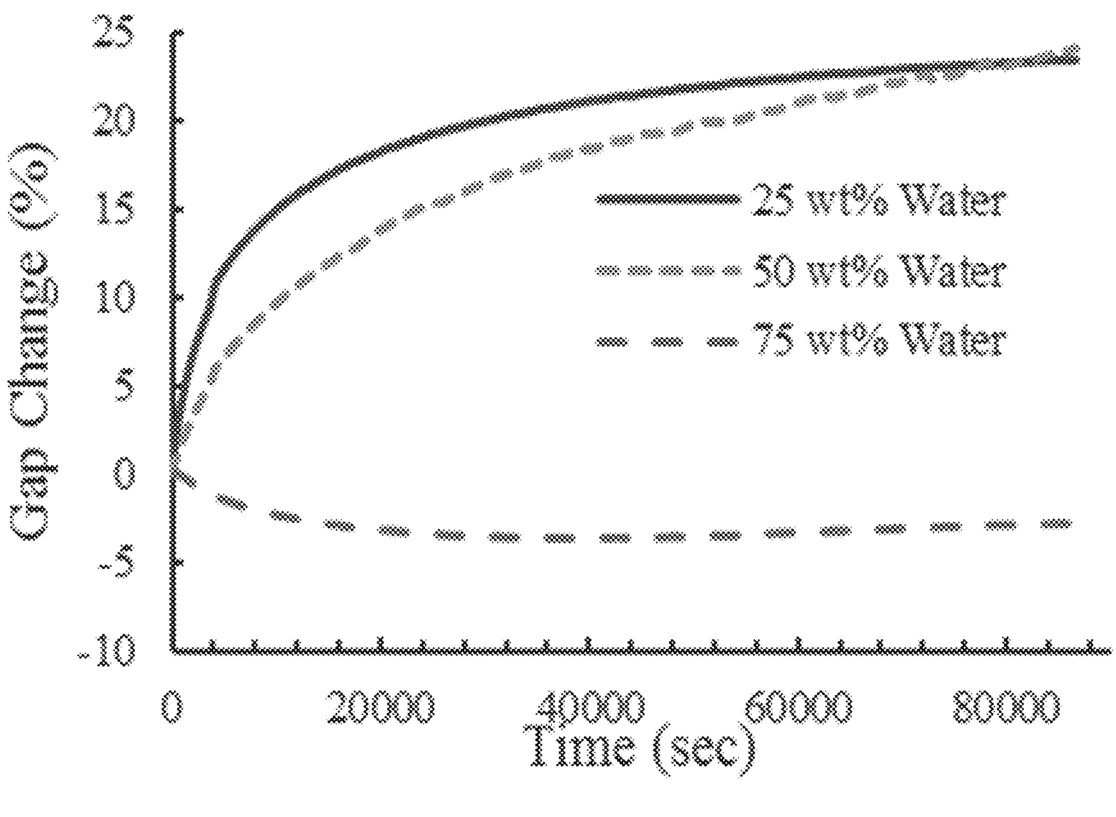
FIG. 8 shows the gap change vs. time for hydrogels of the invention with differing water content.

Swelling the hydrogels under positive normal force demonstrated the ability of hydrogels to swell (FIG. 8) under conditions which mimic the body environment. The gap for hydrogels made with either 25 or 50 wt % water increased by over 20% over the course of 24 h. Lower initial water content led to increased initial swelling, though both the 25 and 50% samples showed similar gaps after 24 h. Hydrogels with higher water content did not swell, but instead the gap decreased slightly.

CT Imaging

Figure 9:
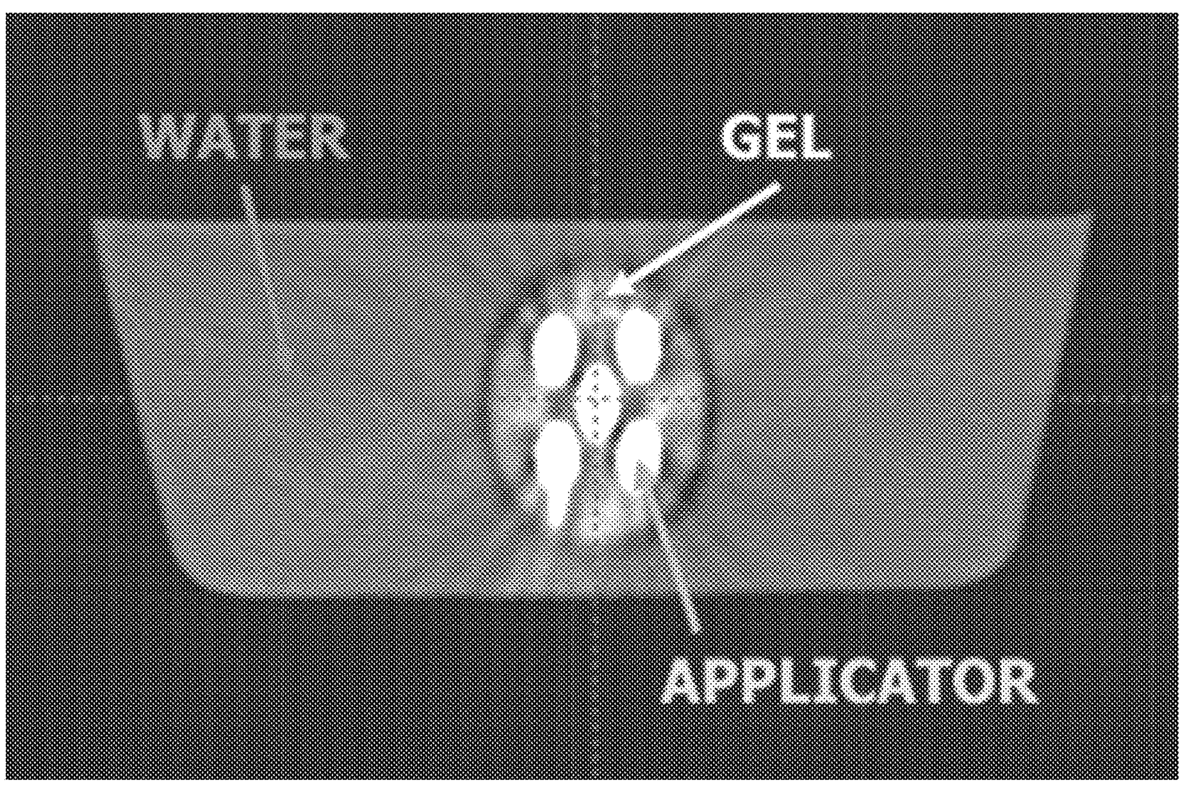
FIG. 9 shows a CT image of an exemplary hydrogel of the invention and exemplary brachytherapy applicator of the invention in a water bath.
Figures 10A, 10B:
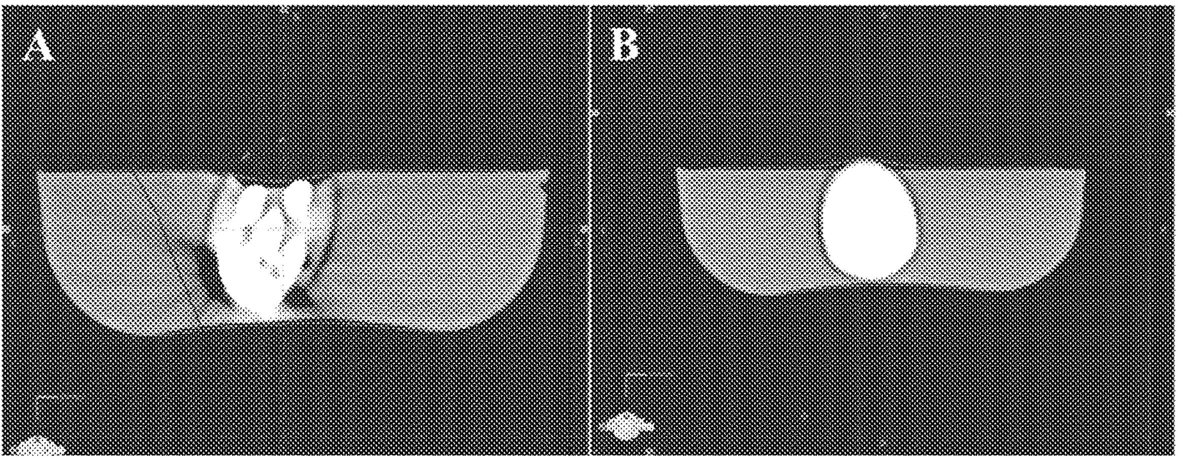
FIG. 10(*a*) shows an CT image of a hydrogel of the invention (1.2:1 thiol:acrylate, 50 wt % $H_2O$, 0.1M $NaHCO_3$) on a 15 mL scale, without a contrast agent.

CT imaging studies demonstrated the hydrogels' distinguishability from water, which served as an analogue for tissue and the metal applicator, a crucial factor for effective image-guided treatment planning. FIG. 9 shows a representative example of the images obtained. The hydrogel displayed a radiation absorption value of 73 H.U., a value significantly higher than water which occurs at approximately 0 H.U. The metal applicator displayed high radiation absorption, with an electron density value of almost 2000 H.U. Addition of a contrast agent to the hydrogel precursor solution (FIG. 10) enabled further tuning of radiation absorption, without perturbing the gel-formation process.

Biological Evaluation

Figure 11:
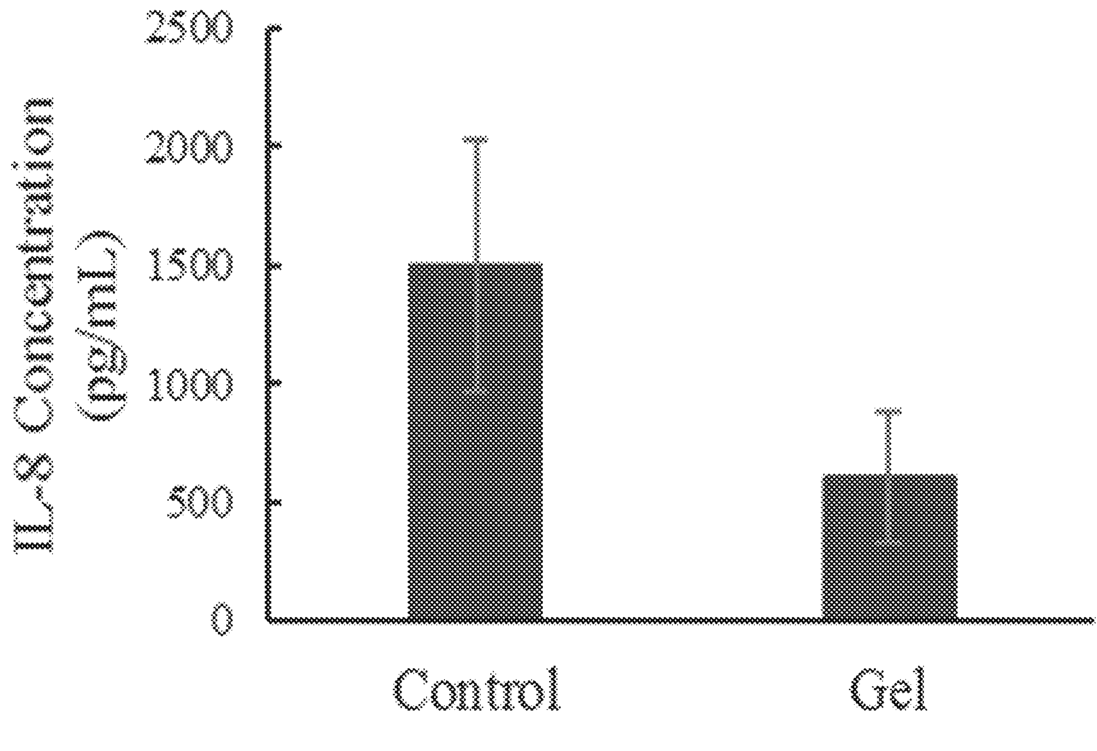
FIG. 11 shows an IL-8 ELISA assay of a control and an exemplary polymeric gel of the invention after 48 h of incubation against hydrogel samples of the invention.

A study of the cytocompatibility of the hydrogel with vaginal epithelial cells demonstrated favorable use for deployment in vivo. Following a 24 h incubation with hydrogels, Cell Titer Glo assay revealed maintenance of cell viability as compared to untreated control cells, with viabilities of 94±32%. Due to the rapid reaction of thiol and acrylate, hydrogels containing these functional groups neglected to cause significant cell toxicity. Additionally, unreacted oligomers in the sol fraction also failed to elucidate significant toxicity. The cytokine IL-8 elucidates an immune response when produced in significant quantities in the human body. VK2/E6E7 vaginal epithelial cells express low levels of IL-8 in control culture, making IL-8 an attractive choice to evaluate potential immune responses. As shown in FIG. 11, vaginal epithelial cells exposed to hydrogel for 48 h exhibited significantly lowered IL-8 concentration than their untreated controls. Despite limited evaluation of potential inflammatory cytokines, a lack of upregulation in IL-8 presents a favorable preliminary immune response.

EXPERIMENTAL DISCUSSION

Hydrogel Formation

Rapid formation of thiol-Michael addition hydrogel of the invention occurred upon mixing the trithiol THIOCURE ETTMP 1300 and PEGDA oligomers in dilute, aqueous $NaHCO_3$. The choice of inexpensive, commercially available THIOCURE and PEGDA as the starting materials facilitated facile scale-up and clinical evaluation. The benign nature of $NaHCO_3$ ensures that no adverse reactions will occur in patients during hydrogel formation and allowed for further gel time tuning simply by altering the concentration of $NaHCO_3$.

The resulting soft hydrogels of the invention show high observed gel fractions, indicating little potential for soluble fractions leaching into the body during treatment. Since any resulting sol fraction primarily consists of PEG, minimal potential for harm exists from their leaching onto the vaginal mucosal surfaces. Rapid gelation ensured deliverable hydrogels on a timescale conducive to clinical application. Hydrogels from $PEGDA_{261}$ showed slower hydrogel-formation behavior, which likely results from the insolubility of $PEGDA_{261}$ in water, as indicated by an initially cloudy solution that formed upon mixing the precursor materials and confirmed by Dynamic Light Scattering. Hydrogels with lower water content formed slowly due to the higher viscosity of the solution and lower catalyst loading. Forming the hydrogels of the invention with a slight stoichiometric excess of thiol resulted in more rapid hydrogel formation. Additional thiol served to compensate for the unavoidable presence of disulfide bridges in the solution which reduced the number of available thiol for reaction. See Jo et al., *J. Biomed. Mater. Res. Part A* 2010, 93A, 870-877.

All hydrogels of the invention reached a shear modulus value of 10 kPa within 10 min. The choice of this value reflects the force of the valsava contraction in the vagina, representing the maximum force the hydrogel will likely encounter in vivo. See Baldwin et al., *Polym. Chem.* 2013, 4(1), 133-143. Though most hydrogels of the invention take up to 15 min to reach their equilibrium modulus value, the time to 10 kPa occurred in as little as 2 min by increasing base concentration to 0.25 M. The benign nature of $NaHCO_3$ should not increase irritation or harm patient outcomes. Once the hydrogel reaches a modulus value of 10 kPa, medical professionals can begin imaging procedures and other clinical preparations despite incomplete hydrogel formation.

Hydrogel Modulus

Most hydrogels of the invention displayed equilibrium moduli compatible with use as a packing material for intracavitary brachytherapy. The hydrogels possess sufficiently high moduli to stabilize the applicator and displace tissue while remaining soft enough for easy and comfortable removal upon delivery. The relative insensitivity of the modulus to formulation conditions likely reflected an interplay of various factors. Theoretical models predicted a dependence of storage modulus on the molecular weight between crosslinks (see Pritchard et al., *Biomaterials* 2011, 32, 587-597; Martin et al., *Polymer* 2008, 49, 1892-1901), however, these models presupposed homogenous, defect-free networks. While many hydrogels formed using step-growth mechanisms form highly homogenous networks (see Nair et al., *Polymer* 2010, 51, 4383-4389), the extremely rapid nature of hydrogel formation of the hydrogel of the invention likely leads to relatively defective network formation. Previous research describes similar defect formation in rapidly forming PEG networks synthesized using free radical methods. See Martin et al., *Polymer* 2008, 49, 1892-1901. A hydrogel with many defects possesses a lower modulus than the theoretical value. See Curro et al., *Macromolecules* 1985, 18, 1157-62; Martin et al., *Polymer* 2008, 49, 1892-1901. The presence of defects coupled with the relatively low differences in theoretical molecular weight between crosslinks likely mitigates any significant effect of PEGDA molecular weight on hydrogel modulus.

Water Absorption

The hydrogels rapidly absorbed water from the dry state, absorbing as much as 150 wt % water in 1 h, and absorbed up to 250 wt % at equilibrium. Hydrogels from $PEGDA_{261}$ showed lower water uptake both after 1 h and at equilibrium, likely due to a denser network due to slower hydrogel-formation, shorter PEG chain length, and an increased weight fraction of hydrophobic β-thioester moieties. Hydrogels form $PEGDA_{513}$ and $PEGDA_{668}$ behaved similarly, with the $PEGDA_{668}$ samples absorbing slightly more water. Increased base concentration increased water absorption slightly. Hydrogels made with 75 wt % water showed high water uptake at equilibrium. Hydrogels with 75 wt % water exceeded the equilibrium water content of most other hydrogel materials tested. An investigation into water absorption from the as-formed, hydrated state revealed increased water uptake with lower initial water content due to the as-formed hydrogels having water contents further from the equilibrium value. Even samples with 50 wt % water absorbed up to 60 wt % water in 1 h, with a volume increase of almost 70 wt %. Performing the swelling under 10 kPa of pressure demonstrated swelling as well. While the swelling occurs slowly under these experimental conditions, the very low surface area experienced limits the rate of diffusion. However, this experiments validates the hydrogels' ability to displace tissue with a 10 kPa modulus. As medical professionals only require small displacements to protect healthy tissue; these volume changes are well-suited for the proposed application.

CT Imaging

Preliminary CT studies revealed hydrogels of the invention are clearly distinguishable from both the brachytherapy applicator and water, which will aid medical professionals in radiation treatment planning. Other experiments (FIG. 10) also demonstrated hydrogel formation in the presence of contrast agent, allowing further tuning of the radiation absorption if necessary. The contrast allows for hydrogel formation, image-guided treatment planning, and treatment delivery in rapid succession.

Biological Evaluation

Biological studies on human vaginal epithelial cells revealed cytocompatibilty for times exceeding those required for vaginal brachytherapy delivery. Selecting vaginal epithelial cells served to provide a cell model closest to the relevant tissue systems. Cell viability assays showed insignificant cytotoxicity when cultured alongside the hydrogels. As these hydrogels remain unextracted during evaluation, these studies also suggested low cytotoxicity of any soluble fractions present in the hydrogel. Due to the complex nature of the vaginal mucosa, an immune response which causes post-treatment irritation remains the most likely hazard. An ELSIA assay of IL-8 cytokines showed no upregulation, suggesting little potential for significant immune response. IL-8 selection followed recommendation from the cell supplier as to the most relevant metabolic products. As this is only one potentially relevant marker, more thorough studies are required to fully demonstrate a lack of immunogenicity though these studies are beyond the scope of the current work and will be reported in the future. However, as Langer and coworkers observed similarly low cytotoxicity and immunogenicity on RAW-blue macrophage cells and hydrogel materials, the likelihood for immunogenicity of the hydrogel is low. See O'Shea et al., *Adv. Mater.* 2015, 27, 65-72. The low observed cytotoxicity and non-immunogenicity demonstrates the suitability of the thiol-Michael-derived hydrogels for vaginal application.

The thiol-Michael reaction enables access to a rapidly-forming hydrogel of the invention for use as a packing material in intracavitary brachytherapy (e.g., pelvic brachytherapy) applications. Initial investigations showed that dilute, aqueous $NaHCO_3$ behaved as a mild, biocompatible, and efficient base to form the hydrogel. Changes in the PEGDA oligomer molecular weight exerted no influence on key properties such as gel time, time to 10 kPa, time to equilibrium plateau modulus, and the final plateau storage modulus. However, changing variables such as initial water content and base concentration allowed for control over hydrogel properties. Formulations involving $PEGDA_{668}$ and 0.25 M $NaHCO_3$ at 50 wt % water demonstrated ideal behavior for application in a brachytherapy context with a modulus of moderate magnitude that form acceptably rapidly. Preliminary imaging studies revealed high amenability of the hydrogel materials to image-guided brachytherapy procedures. The invention's novel application of hydrogel technology will significantly enhance the customizability and patient comfort of intracavitary brachytherapy (e.g., pelvic brachytherapy) application, allowing for vastly improved patient outcomes.

The claimed invention is:

1. A method providing pelvic brachytherapy, comprising:

providing a brachytherapy applicator comprising a therapy delivery portion with one or more radioactive sources attached thereto, positioning the brachytherapy applicator at a static position in a pelvic cavity of the body, providing at least one container, positioning the at least one container inside the pelvic cavity, delivering a thiol-Michael addition hydrogel to the inside of the at least one container present inside the pelvic cavity, expanding the thiol-Michael addition hydrogel inside of the at least one container present inside the pelvic cavity to conform the at least one container to the pelvic cavity, displacing tissue and/or organs by the expanding thiol-Michael addition hydrogel, delivering the one or more radioactive sources to a target tissue region, optionally lowering the modulus of the thiol-Michael addition hydrogel inside of the at least one container present inside the pelvic cavity, and optionally extracting from the pelvic cavity the brachytherapy applicator and/or the at least one container that contains the thiol-Michael addition hydrogel, wherein the pelvic cavity is a vagina or a uterus.

2. The method of claim 1, wherein the thiol-Michael addition hydrogel comprises two or more precursor materials delivered separately to the inside of the at least one container present inside the pelvic cavity.

3. The method of claim 1, wherein the thiol-Michael addition hydrogel comprises two or more precursor materials, and wherein the two or more precursor materials are reacted inside of the at least one container present inside the pelvic cavity to form the thiol-Michael addition hydrogel.

4. The method of claim 1, wherein the delivering of the thiol-Michael addition hydrogel to the inside of the at least one container present inside the pelvic cavity step comprises forming the thiol-Michael addition hydrogel inside of the at least one container present inside the pelvic cavity.

5. The method of claim 1, wherein the tissue and/or organs are displaced away from one or more radioactive sources attached to the brachytherapy applicator.

6. The method of claim 1, wherein the thiol-Michael addition hydrogel inside of the at least one container present inside the pelvic cavity is expanded by adding water and/or saline solution to the gel.

7. The method of claim 1, wherein the modulus of the thiol-Michael addition hydrogel inside of the at least one container present inside the pelvic cavity is lowered by adding water or saline solution to the gel in an amount sufficient to lower the modulus of the thiol-Michael addition hydrogel.

8. The method of claim 1, wherein the at least one container surrounds the brachytherapy applicator inside the pelvic cavity.

9. The method of claim 1, wherein the brachytherapy applicator is a ring and tandem applicator, tandem and ovoid applicator, Y-applicator, intrauterine tandems applicator, brachytherapy needle applicator, or any other pelvic brachytherapy applicator designed to treat via intracavitary or interstitial methods.

10. The method of claim 1, wherein the thiol-Michael addition hydrogel comprises the reaction product of at least one Michael acceptor and at least one thiol compound, reacted in the presence of an aqueous base.

11. The method of claim 10, wherein the at least one Michael acceptor is selected from the group consisting of acrylate, vinyl nitrile, vinyl nitro, vinyl phosphonate, vinyl sulfonate, enone compounds, and mixtures thereof.

12. The method of claim 11, wherein the at least one Michael acceptor is selected from an oligomeric poly(ethylene glycol) diacrylate.

13. The method of claim 10, wherein the at least one thiol compound is selected from the group consisting of a multi-arm, thiol terminated polymer with a backbone consisting of poly(ethylene glycol), polycaprolactam, poly(propylene glycol), or poly(lactide) chains, water-soluble polysaccharide functionalized with 3 or more thiol groups per chain, and mixtures thereof.

14. The method of claim 13, wherein the at least one thiol compound is selected from a multi-arm, thiol-terminated PEG oligomer.

15. The method of claim 10, wherein the at least one Michael acceptor is selected from an oligomeric polyethylene glycol diacrylate and the at least one thiol compound is selected from a multi-arm, thiol-terminated PEG oligomer, and the oligomeric polyethylene glycol diacrylate and the multi-arm, thiol-terminated PEG oligomer are reacted in a 1:1 thiol:acrylate stoichiometric ratio.

16. The method of claim 10, wherein the at least one Michael acceptor is selected from an oligomeric polyethylene glycol diacrylate and the at least one thiol compound is selected from a multi-arm, thiol-terminated PEG oligomer, and an excess of the multi-arm, thiol-terminated PEG oligomer is reacted with the oligomeric polyethylene glycol diacrylate.

17. The method of claim 1, wherein the brachytherapy applicator is positioned inside the pelvic cavity before, at the same time, or after the at least one container is positioned inside the pelvic cavity.

18. The method of claim 1, wherein the thiol-Michael addition hydrogel has a modulus between about 10 and about 100 kPa.

19. The method of claim 1, wherein the thiol-Michael addition hydrogel reaches a modulus of about 10 kPa in under 2 minutes in the at least one container present inside the pelvic cavity.

20. The method of claim 1, wherein the brachytherapy applicator is provided in a fixed-geometry.

21. The method of claim 1, wherein the brachytherapy applicator is extracted from the body cavity before the at least one container that contains the thiol-Michael addition hydrogel is extracted from the body cavity.

22. The method of claim 1, wherein the at least one container that contains the thiol-Michael addition hydrogel is extracted from the body cavity before the brachytherapy applicator is extracted from the body cavity.

* * * * *